United States Patent
Wagman et al.

(10) Patent No.: US 6,989,382 B2
(45) Date of Patent: Jan. 24, 2006

(54) CARBOCYCLE BASED INHIBITORS OF GLYCOGEN SYNTHASE KINASE 3

(75) Inventors: Allan S. Wagman, Belmont, CA (US); Sharadha Subramanian, San Ramon, CA (US); John M. Nuss, Danville, CA (US)

(73) Assignee: Chiron Corporation, Emeryville, CA (US)

( * ) Notice: Subject to any disclaimer, the term of this patent is extended or adjusted under 35 U.S.C. 154(b) by 192 days.

(21) Appl. No.: 10/690,497

(22) Filed: Oct. 20, 2003

(65) Prior Publication Data

US 2004/0138273 A1    Jul. 15, 2004

Related U.S. Application Data

(60) Provisional application No. 60/420,432, filed on Oct. 21, 2002.

(51) Int. Cl.
*C07D 401/04*    (2006.01)
*A61K 31/44*    (2006.01)

(52) U.S. Cl. .................. 514/253.01; 544/360; 546/304; 546/307; 514/352

(58) Field of Classification Search .......... 514/253.01, 514/352; 546/304, 307; 544/360
See application file for complete search history.

(56) References Cited

U.S. PATENT DOCUMENTS 3,755,383 A    8/1973    Feit et al.
5,521,192 A    5/1996    Henrie, II et al.

FOREIGN PATENT DOCUMENTS

| EP | 0 857 721 A1 | 8/1998 |
| JP | 4-217647 A | 8/1992 |
| WO | WO 00/18721 A1 | 4/2000 |
| WO | WO 01/70726 A1 | 9/2001 |
| WO | WO 01/70727 A1 | 9/2001 |
| WO | WO 01/78723 A1 | 10/2001 |
| WO | WO 01/81316 A2 | 11/2001 |
| WO | WO 02/20495 A2 | 3/2002 |

*Primary Examiner*—Zinna Northington Davis
(74) *Attorney, Agent, or Firm*—Young J. Suh; Dennis K. Shelton; Alisa A. Harbin

(57) ABSTRACT

New carbocyclic compounds, compositions and methods of inhibiting the activity of glycogen synthase kinase (GSK3) in vitro and of treatment of GSK3 mediated disorders in vivo are provided. The methods, compounds and compositions of the invention may be employed alone, or in combination with other pharmacologically active agents in the treatment of disorders mediated by GSK3 activity, such as in the treatment of diabetes, Alzheimer's disease, other neurodegenerative disorders, such as Parkinson's disease and Huntington's disease, obesity, atherosclerotic cardiovascular disease, essential hypertension, polycystic ovary syndrome, syndrome X, ischemia, traumatic brain injury, bipolar disorder, immunodeficiency or cancer.

40 Claims, No Drawings

CARBOCYCLE BASED INHIBITORS OF GLYCOGEN SYNTHASE KINASE 3

CROSS-REFERENCE TO RELATED APPLICATION

This application claims the benefit of U.S. Provisional Application 60/420,432 filed Oct. 21, 2002.

FIELD OF THE INVENTION

This invention relates to carbocyclic compounds that inhibit the activity of glycogen synthase kinase 3 (GSK3), to pharmaceutical compositions containing the compounds and to the use of the compounds and compositions, alone or in combination with other pharmaceutically active agents. The compounds and compositions provided by the present invention have utility in the treatment of disorders mediated by GSK3 activity, such as diabetes, Alzheimer's disease, other neurodegenerative disorders, such as Parkinson's disease and Huntington's disease, obesity, atherosclerotic cardiovascular disease, essential hypertension, polycystic ovary syndrome, syndrome X, ischemia, especially cerebral ischemia, traumatic brain injury, bipolar disorder, immunodeficiency and cancer.

BACKGROUND OF THE INVENTION

Glycogen synthase kinase 3 (GSK3) is a serine/threonine kinase for which two isoforms, $\alpha$ and $\beta$, have been identified. Woodgett, *Trends Biochem. Sci.*, 16:177–81 (1991). Both GSK3 isoforms are constitutively active in resting cells. GSK3 was originally identified as a kinase that inhibits glycogen synthase by direct phosphorylation. Upon insulin activation, GSK3 is inactivated, thereby allowing the activation of glycogen synthase and possibly other insulin-dependent events, such glucose transport. Subsequently, it has been shown that GSK3 activity is also inactivated by other growth factors that, like insulin, signal through receptor tyrosine kinases (RTKs). Examples of such signaling molecules include IGF-1 and EGF. Saito et al., *Biochem. J.*, 303:27–31 (1994); Welsh et al., *Biochem. J.* 294:625–29 (1993); and Cross et al., *Biochem. J.*, 303:21–26 (1994).

Agents that inhibit GSK3 activity are useful in the treatment of disorders that are mediated by GSK3 activity. In addition, inhibition of GSK3 mimics the activation of growth factor signaling pathways and consequently GSK3 inhibitors are useful in the treatment of diseases in which such pathways are insufficiently active. Examples of diseases that can be treated with GSK3 inhibitors are described below.

Diabetes

Type 2 diabetes is an increasingly prevalent disease of aging. It is initially characterized by decreased sensitivity to insulin and a compensatory elevation in circulating insulin concentrations, the latter of which is required to maintain normal blood glucose levels. Increased insulin levels are caused by increased secretion from the pancreatic beta cells, and the resulting hyperinsulinemia is associated with cardiovascular complications of diabetes. As insulin resistance worsens, the demand on the pancreatic beta cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure and blindness. The exact mechanism(s) causing type 2 diabetes are unknown, but result in impaired glucose transport into skeletal muscle and increased hepatic glucose production, in addition to inadequate insulin response. Dietary modifications are often ineffective, therefore the majority of patients ultimately require pharmaceutical intervention in an effort to prevent and/or slow the progression of the complications of the disease. Many patients can be treated with one or more of the many oral anti-diabetic agents available, including sulfonylureas, to increase insulin secretion. Examples of sulfonylurea drugs include metformin for suppression of hepatic glucose production, and troglitazone, an insulin-sensitizing medication. Despite the utility of these agents, 30–40% of diabetics are not adequately controlled using these medications and require subcutaneous insulin injections. Additionally, each of these therapies has associated side effects. For example, sulfonylureas can cause hypoglycemia and troglitazone can cause severe hepatoxicity. Presently, there is a need for new and improved drugs for the treatment of prediabetic and diabetic patients.

As described above, GSK3 inhibition stimulates insulin-dependent processes and is consequently useful in the treatment of type 2 diabetes. Recent data obtained using lithium salts provides evidence for this notion. The lithium ion has recently been reported to inhibit GSK3 activity. Klein et al., *PNAS* 93:8455–9 (1996). Since 1924, lithium has been reported to have antidiabetic effects including the ability to reduce plasma glucose levels, increase glycogen uptake, potentiate insulin, up-regulate glucose synthase activity and to stimulate glycogen synthesis in skin, muscle and fat cells. However, lithium has not been widely accepted for use in the inhibition of GSK3 activity, possibly because of its documented effects on molecular targets other than GSK3. The purine analog 5-iodotubercidin, also a GSK3 inhibitor, likewise stimulates glycogen synthesis and antagonizes inactivation of glycogen synthase by glucagon and vasopressin in rat liver cells. Fluckiger-Isler et al., *Biochem J* 292:85–91 (1993); and Massillon et al., *Biochem J* 299:123–8 (1994). However, this compound has also been shown to inhibit other serine/threonine and tyrosine kinases. Massillon et al., *Biochem J* 299:123–8 (1994).

Alzheimer's Disease

GSK3 is also involved in biological pathways relating to Alzheimer's disease (AD). The characteristic pathological features of AD are extracellular plaques of an abnormally processed form of the amyloid precursor protein (APP), so called $\beta$-amyloid peptide ($\beta$-AP) and the development of intracellular neurofibrillary tangles containing paired helical filaments (PHF) that consist largely of hyperphosphorylated tau protein. GSK3 is one of a number of kinases that have been found to phosphorylate tau protein in vitro on the abnormal sites characteristic of PHF tau, and is the only kinase also demonstrated to do this in living cells and in animals. Lovestone et al., *Current Biology.* 4:1077–86 (1994); and Brownlees et al., *Neuroreport* 8: 3251–3255 (1997). Furthermore, the GSK3 kinase inhibitor, LiCl, blocks tau hyperphosphorylation in cells. Stambolic et al., *Current Biology* 6:1664–8 (1996). Thus GSK3 activity may contribute to the generation of neurofibrillary tangles and consequently to disease progression. Recently it has been shown that GSK3$\beta$ associates with another key protein in AD pathogenesis, presenillin 1 (PS1). Takashima et al., *PNAS* 95:9637–9641 (1998). Mutations in the PS1 gene lead to increased production of $\beta$-AP, but the authors also demonstrate that the mutant PS1 proteins bind more tightly to GSK3β and potentiate the phosphorylation of tau, which is bound to the same region of PS1.

Interestingly it has also been shown that another GSK3 substrate, β-catenin, binds to PS1. Zhong et al., *Nature* 395:698–702 (1998). Cytosolic β-catenin is targeted for degradation upon phosphorylation by GSK3 and reduced β-catenin activity is associated with increased sensitivity of neuronal cells to β-AP induced neuronal apoptosis. Consequently, increased association of GSK3β with mutant PS1 may account for the reduced levels of β-catenin that have been observed in the brains of PS1 mutant AD patients and to the disease related increase in neuronal cell-death. Consistent with these observations, it has been shown that injection of GSK3 antisense but not sense, blocks the pathological effects of β-AP on neurons in vitro, resulting in a 24 hr delay in the onset of cell death and increased cell survival at 1 hr from 12 to 35%. Takashima et al., *PNAS* 90:7789–93. (1993). In these latter studies, the effects on cell-death are preceded (within 3–6 hours of β-AP administration) by a doubling of intracellular GSK3 activity, suggesting that in addition to genetic mechanisms that increase the proximity of GSK3 to its substrates, β-AP may actually increase GSK3 activity. Further evidence for a role for GSK3 in AD is provided by the observation that the protein expression level (but, in this case, not specific activity) of GSK3 is increased by 50% in postsynaptosomal supernatants of AD vs. normal brain tissue. Pei et al., *J Neuropathol Exp* 56:70–78 (1997).

Even more recently, it has been shown that therapeutic concentrations of lithium, a known GSK3 inhibitor, block the production of β-AP by interfering with amyloid precursor protein (APP) cleavage. Phiel et al., *Nature* 423(22): 435–438 (2003). Since GSK3 also phosphorylates tau protein, the principal component of neurofibrillary tangles, inhibition of GSK3 provides both a reduction in amyloid plaques and neurofibrillary tangles, and is useful in the treatment of Alzheimer's disease.

Other CNS Disorders

In addition to the effects of lithium described above, there is a long history of the use of lithium to treat bipolar disorder (manic depressive syndrome). This clinical response to lithium may reflect an involvement of GSK3 activity in the etiology of bipolar disorder, in which case GSK3 inhibitors could be relevant to that indication. In support of this notion it was recently shown that valproate, another drug commonly used in the treatment of bipolar disorder, is also a GSK3 inhibitor. Chen et al., *J. Neurochemistry* 72:1327–1330 (1999). One mechanism by which lithium and other GSK3 inhibitors may act to treat bipolar disorder is to increase the survival of neurons subjected to aberrantly high levels of excitation induced by the neurotransmitter, glutamate. Nonaka et al., *PNAS* 95: 2642–2647 (1998). Glutamate-induced neuronal excitotoxicity is also believed to be a major cause of neurodegeneration associated with acute damage, such as in cerebral ischemia, traumatic brain injury and bacterial infection. Furthermore it is believed that excessive glutamate signaling is a factor in the chronic neuronal damage seen in diseases such as Alzheimer's, Huntingdon's, Parkinson's, AIDS associated dementia, amyotrophic lateral sclerosis (AML) and multiple sclerosis (MS). Thomas, *J. Am. Geriatr. Soc.* 43: 1279–89 (1995). Consequently GSK3 inhibitors are believed to be a useful treatment in these and other neurodegenerative disorders.

Immune Potentiation

GSK3 phosphorylates transcription factor NF-AT, and promotes its export from the nucleus, in opposition to the effect of calcineurin. Beals et al., *Science* 275:1930–33 (1997). Thus, GSK3 blocks early immune response gene activation via NF-AT, and GSK3 inhibitors may tend to permit or prolong activation of immune responses. Thus GSK3 inhibitors are believed to prolong and potentiate the immunostimulatory effects of certain cytokines, and such an effect may enhance the potential of those cytokines for tumor immunotherapy or indeed for immunotherapy in general.

Other Disorders

Lithium also has other biological effects. It is a potent stimulator of hematopoiesis, both in vitro and in vivo. Hammond et al., *Blood* 55: 26–28 (1980). In dogs, lithium carbonate eliminated recurrent neutropenia and normalized other blood cell counts. Doukas et al. *Exp Hematol* 14: 215–221 (1986). If these effects of lithium are mediated through the inhibition of GSK3, then GSK3-specific inhibitors may have even broader therapeutic applications.

Since inhibitors of GSK3 are useful in the treatment of many diseases, the identification of new inhibitors of GSK3 would be highly desirable.

SUMMARY OF THE INVENTION

It has now been surprisingly discovered that glycogen synthase kinase 3 (GSK3) activity can be inhibited in vitro or in vivo by certain carbocycle based derivatives provided by the present invention. The carbocycle derivatives of the invention have been found to possess specificity for GSK3. Accordingly, the present invention provides new compounds, compositions and methods of inhibiting the activity of GSK3 in vitro and of treatment of GSK3 mediated disorders in vivo. In one aspect, the present invention provides new compounds having GSK3 inhibition activity of the following formula (I):

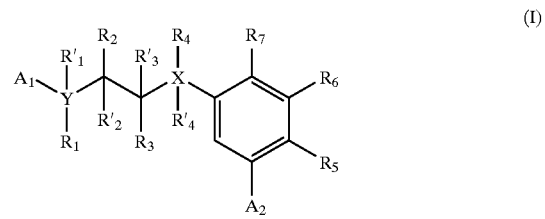

wherein:

X and Y are independently selected from the group consisting of nitrogen, oxygen, and optionally substituted carbon;

$A_1$ and $A_2$ are optionally substituted aryl, arylamino, aryloxy or heteroaryl;

$R_1$, $R_2$, $R_3$ and $R_4$ are independently selected from the group consisting of hydrogen, hydroxyl, and optionally substituted loweralkyl, cycloloweralkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;

$R'_1$, $R'_2$, $R'_3$ and $R'_4$ are independently selected from the group consisting of hydrogen, and optionally substituted loweralkyl;

$R_5$, $R_6$ and $R_7$ are independently selected from the group consisting of hydrogen, hydroxy, halo, carboxyl, nitro, amino, amido, amidino, imido, cyano, and substituted or unsubstituted loweralkyl, loweralkoxy, alkylcarbonyl, arylcarbonyl, aralkylcarbonyl, heteroarylcarbonyl, heteraralkylcarbonyl, alkylcarbonyloxy, arylcarbonyloxy, aralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, arylamino, aralkylamino, heteroarylamino, heteroaralkylamino, alkylcarbonylamino, alkylaminocarbonylamino, arylaminocarbonylamino, aralkylcarbonylamino, heteroaralkylcarbonylamino, arylcarbonylamino, heteroarylcarbonylamino, amidino, cycloalkyl, cycloamido, cyclothioamido, cycloamidino, heterocyclyl, heterocycloamidino, cycloimido, heterocycloimido, guanidinyl, aryl, biaryl, heteroaryl, heterobiaryl, heterocyclo, heterocycloalkyl, arylsulfonyl and arylsulfonamido;

and the pharmaceutically acceptable salts thereof.

The methods, compounds and compositions of the invention may be employed alone, or in combination with other pharmacologically active agents in the treatment of disorders mediated by GSK3 activity, such as in the treatment of diabetes, Alzheimer's disease, other neurodegenerative disorders, such as Parkinson's disease and Huntington's disease, obesity, atherosclerotic cardiovascular disease, essential hypertension, polycystic ovary syndrome, syndrome X, ischemia, especially cerebral ischemia, traumatic brain injury, bipolar disorder, immunodeficiency or cancer.

DETAILED DESCRIPTION OF THE PREFERRED EMBODIMENT

In accordance with the present invention, compounds, compositions and methods are provided for the inhibition of glycogen synthase kinase 3 (GSK3) activity, either in vitro or in vivo. In one aspect, the present invention provides new compounds having GSK3 inhibition activity of the following formula (I):

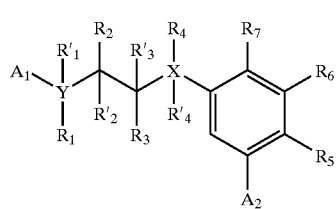

(I)

wherein:

X and Y are independently selected from the group consisting of nitrogen, oxygen, and optionally substituted carbon;

$A_1$ and $A_2$ are optionally substituted aryl, arylamino, aryloxy or heteroaryl;

$R_1$, $R_2$, $R_3$ and $R_4$ are independently selected from the group consisting of hydrogen, hydroxyl, and optionally substituted loweralkyl, cycloloweralkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;

$R'_1$, $R'_2$, $R'_3$ and $R'_4$ are independently selected from the group consisting of hydrogen, and optionally substituted loweralkyl;

$R_5$, $R_6$ and $R_7$ are independently selected from the group consisting of hydrogen, hydroxy, halo, carboxyl, nitro, amino, amido, amidino, imido, cyano, and substituted or unsubstituted loweralkyl, loweralkoxy, alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, arylamino, aralkylamino, heteroarylamino, heteroaralkylamino, alkylcarbonylamino, alkylaminocarbonylamino, arylaminocarbonylamino, aralkylcarbonylamino, heteroaralkylcarbonylamino, arylcarbonylamino, heteroarylcarbonylamino, amidino, cycloalkyl, cycloamido, cyclothioamido, cycloamidino, heterocyclyl, heterocycloamidino, cycloimido, heterocycloimido, guanidinyl, aryl, biaryl, heteroaryl, heterobiaryl, heterocyclo, heterocycloalkyl, arylsulfonyl and arylsulfonamido;

and the pharmaceutically acceptable salts thereof.

In one presently preferred embodiment of the invention, at least one of X and Y is nitrogen. Representative compounds of this group include those compounds in which one of X and Y is nitrogen and the other of X and Y is oxygen or optionally substituted carbon. Preferably, both X and Y are nitrogen.

The constituents $A_1$ and $A_2$ may independently comprise an aromatic ring having from 3 to 10 carbon ring atoms and optionally 1 or more ring heteroatoms. Thus, in one embodiment, $A_1$ and/or $A_2$ can be optionally substituted carbocyclic aryl, arylamino or aryloxy, such as, for example, substituted or unsubstituted phenyl, phenylamino, phenyloxy. Alternatively, $A_1$ and/or $A_2$ are optionally substituted heteroaryl, such as, for example, substituted or unsubstituted pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, which may substituted with at least one and not more than 3 substitution groups. Representative substitution groups can be independently selected from the group consisting of, for example, nitro, amino, cyano, halo, thioamido, amidino, oxamidino, alkoxyamidino, imidino, guanidino, sulfonamido, carboxyl, formyl, loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aminoalkyl and cyanoalkyl.

In other embodiments of the invention at least one of $R_1$, $R_2$, $R_3$ and $R_4$ may be hydrogen, or unsubstituted or substituted loweralkyl selected from the group consisting of haloloweralkyl, heterocycloaminoalkyl, and loweralkylaminoloweralkyl. Presently preferred embodiments of the invention include compounds wherein $R_1$, $R_2$, and $R_3$ are hydrogen and $R_4$ is selected from the group consisting of hydrogen, methyl, ethyl, aminoethyl, dimethylaminoethyl, pyridylethyl, piperidinyl, pyrrolidinylethyl, piperazinylethyl and morpholinylethyl.

The constituent $A_1$ can be an aromatic ring having from 3 to 10 carbon ring atoms and optionally 1 or more ring heteroatoms. Thus, in one embodiment, $A_1$ can be optionally substituted carbocyclic aryl. Alternatively, $A_1$ is optionally substituted heteroaryl, such as, for example, substituted or unsubstituted pyridyl, pyrimidinyl thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, which may substituted with at least one and not more than 3 substitution groups. Representative substitution groups can be independently selected from the group consisting of, for example, nitro, amino, cyano, halo, thioamido, amidino, oxamidino, alkoxyamidino, imidino, guanidino, sulfonamido, carboxyl, formyl, loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aminoalkyl and cyanoalkyl.

In a presently particularly preferred embodiment of the invention, $A_1$ has the formula:

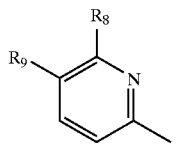

(II)

wherein $R_8$ and $R_9$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl. Most preferably, $A_1$ is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl.

Other presently preferred compounds of the invention include compounds of formula (I) wherein at least one of $R_5$, $R_6$ and $R_7$ is selected from the group consisting of substituted and unsubstituted aryl, heteroaryl and biaryl. In presently preferred embodiments, at least one of $R_5$, $R_6$ and $R_7$ is a substituted or unsubstituted moiety of the formula:

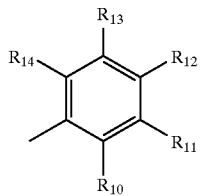

(III)

wherein $R_{10}$, $R_{11}$, $R_{12}$, $R_{13}$, and $R_{14}$ are independently selected from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, alkylthio, alkylcarbonylamino, aralkylcarbonylamino, heteroaralkylcarbonylamino, arylcarbonylamino, heteroarylcarbonylamino, aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyloxyalkyl, and heteroaralkcarbonyloxyalkyl. Presently particularly preferred compounds are obtained wherein $R_{10}$, $R_{11}$, $R_{13}$, and $R_{14}$ are hydrogen and $R_{12}$ is selected from the group consisting of halo, loweralkyl, hydroxy, loweralkoxy, haloloweralkyl, aminocarbonyl, alkylaminocarbonyl, morpholino, piperidino and cyano; $R_{11}$, $R_{13}$, and $R_{14}$ are hydrogen and $R_{10}$ and $R_{12}$ are independently selected from the group consisting of halo, loweralkyl, hydroxy, loweralkoxy, haloloweralkyl, morpholino, piperidino and cyano; $R_{10}$, $R_{11}$, $R_{13}$, and $R_{14}$ are hydrogen and $R_{12}$ is heteroaryl; $R_{10}$, $R_{11}$, $R_{13}$, and $R_{14}$ are hydrogen and $R_{12}$ is a heterocycloalkyl; and wherein at least one of $R_{10}$, $R_{11}$, $R_{12}$, $R_{13}$, and $R_{14}$ are halo and the remainder of $R_{10}$, $R_{11}$, $R_{12}$, $R_{13}$, and $R_{14}$ are hydrogen. Preferably, at least one of $R_5$ and $R_7$ is selected from the group consisting of chlorophenyl, dichlorophenyl, fluorophenyl, difluorophenyl, bromophenyl, dichlorofluorophenyl, trifluoromethylphenyl, chlorofluorophenyl, bromochlorophenyl, bromofluorophenyl, ethylphenyl, methylchlorophenyl, ethylchlorophenyl, imidazolylphenyl, cyanophenyl, morphlinophenyl and cyanochlorophenyl.

In representative embodiments of the invention, $R_5$, $R_6$ and $R_7$ may be substituted alkyl, such as, for example, aralkyl, hydroxyalkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl; substituted amino such as alkylamino, alkylcarbonylamino, alkoxycarbonylamindo, arylalkylamino, arylcarbonylamino, alkylthiocarbonylamino, arylsulfonylamino, heteroarylamino, alkylcarbonylamino, arylcarbonylamino, heteroarylcarbonylamino, aralkylcarbonylamino, and heteroaralkylcarbonylamino; or substituted carbonyl such as unsubstituted or substituted aminocarbonyl, alkyloxycarbonyl, aryloxycarbonyl, aralkyloxycarbonyl and alkylaminoalkyloxycarbonyl. In other embodiments, $R_6$ may be selected from the group consisting of amidino, guanidino, cycloimido, heterocycloimido, cycloamido, heterocycloamido, cyclothioamido and heterocycloloweralkyl. In yet other embodiments, at least one of $R_5$, $R_6$ and $R_7$ may be aryl, heteroaryl, or heterocyclyl such as, for example, substituted or unsubstituted pyridyl, pyrimidinyl, pyrrolidinyl, pyrrolinyl, pyrazinyl, thiazolyl, indolyl, imidazolyl, imidazolidinyl, oxadiazolyl, oxazolidinyl, oxazolidinonyl, tetrazolyl, pyrazinyl, pyrazolidinyl, piperidyl, piperazinyl, morpholinyl, triazolyl, thienyl, furanyl, quinolinyl, pyrrolyopyridyl, pyrazolonyl, pyridazinyl, benzothiazolyl, benzopyridyl, benzotriazolyl, and benzimidazolyl. In yet other embodiments, at least one of $R_5$, $R_6$ and $R_7$ may be a monoketopiperazinyl group having the structure:

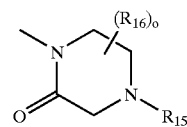

(IV)

wherein $R_{15}$ and $R_{16}$ are independently selected from the group consisting of hydrogen, loweralkyl, loweralkynyl, aryl, heteroaryl, arylloweralkyl, loweralkylarylloweralkyl, haloloweralkyl, haloarylloweralkyl carbocyclic and heterocyclic; or $R_8$ can be taken with another $R_{16}$ or with $R_{15}$ to form a carbocyclic, heterocyclic or aryl ring; and o is an integer between 1 and 3. In representative embodiments of this aspect of the invention, $R_{15}$ is loweralkyl, such as methyl, ethyl, n-propyl, isopropyl, cyclopropyl, n-butyl, iso-butyl or t-butyl, or $R_{15}$ is taken with $R_{16}$ to form a group having the structure:

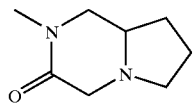
(V)

or

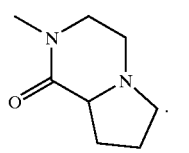
(VI)

As used herein, other representative heterocyclo groups include, for example, those shown below (where the point of attachment of the substituent group, and the other substituent groups shown below, is through the upper left-hand bond). These heterocyclo groups can be further substituted and may be attached at various positions as will be apparent to those having skill in the organic and medicinal chemistry arts in conjunction with the disclosure herein.

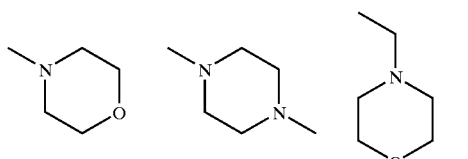

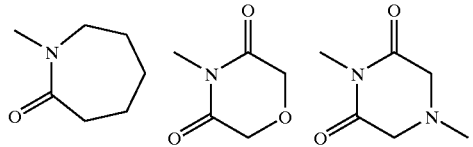

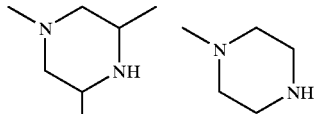

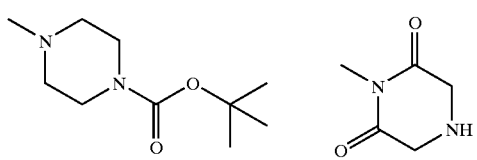

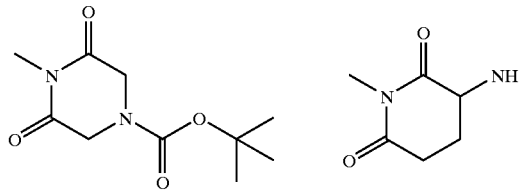

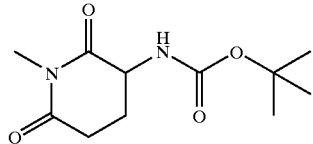

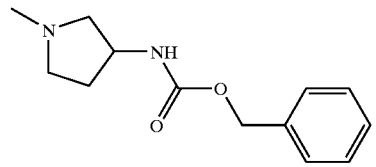

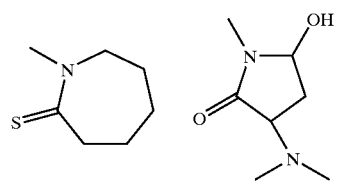

Representative heteroaryl groups include, for example, those shown below. These heteroaryl groups can be further substituted and may be attached at various positions as will be apparent to those having skill in the organic and medicinal chemistry arts in conjunction with the disclosure herein.

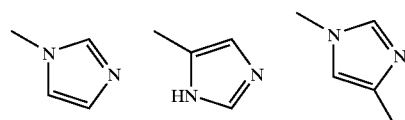

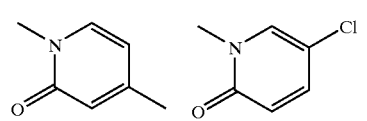

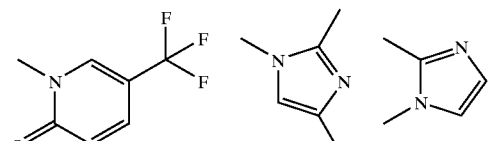

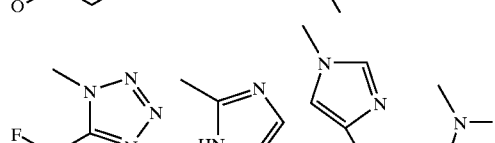

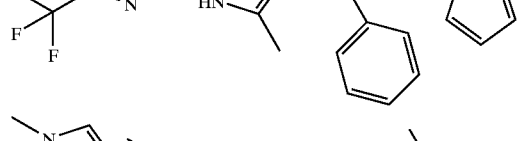

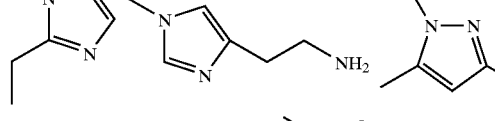

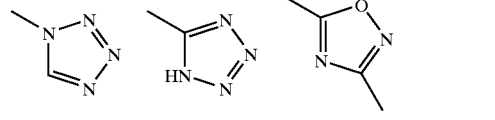

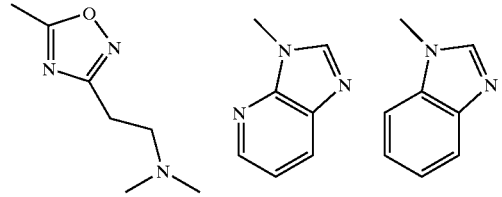

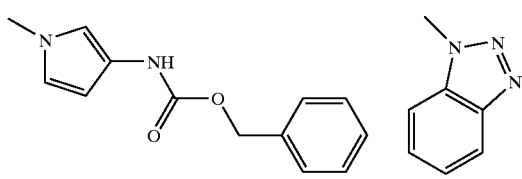

Representative cycloimido and heterocycloimido groups include, for example, those shown below. These cycloimido and heterocycloimido can be further substituted and may be attached at various positions as will be apparent to those having skill in the organic and medicinal chemistry arts in conjunction with the disclosure herein.

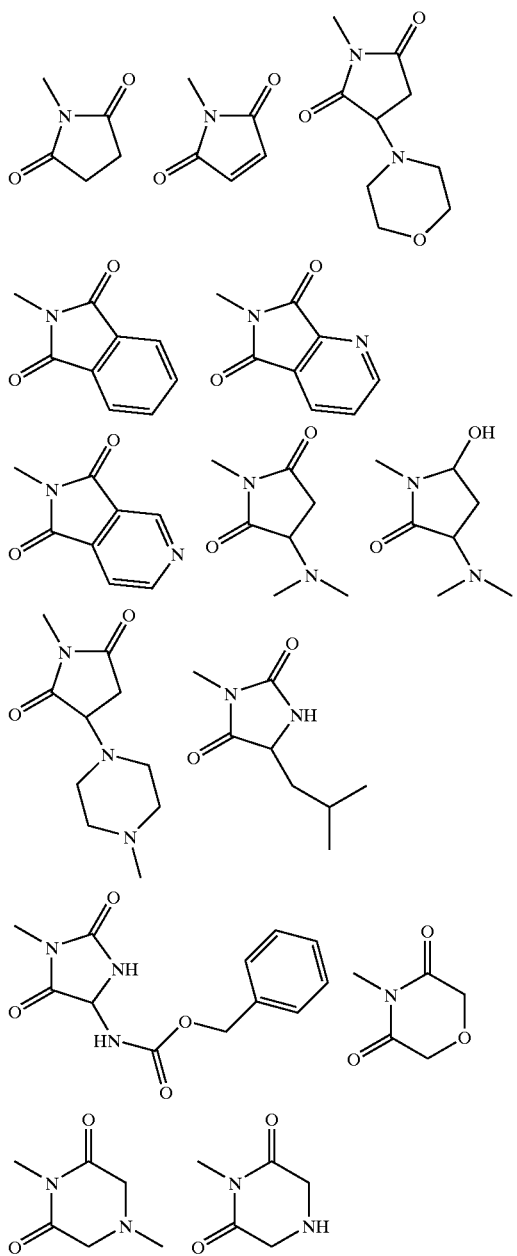

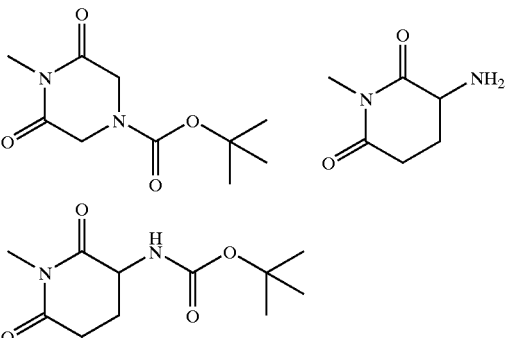

Representative substituted amidino and heterocycloamidino groups include, for example, those shown below. These amidino and heterocycloamidino groups can be further substituted as will be apparent to those having skill in the organic and medicinal chemistry arts in conjunction with the disclosure herein.

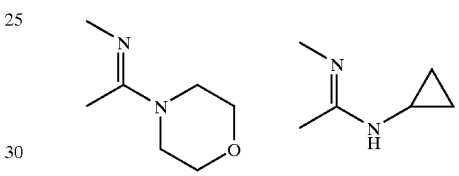

Representative substituted alkylcarbonylamino, alkyloxycarbonylamino, aminoalkyloxycarbonylamino, and arylcarbonylamino groups include, for example, those shown below. These groups can be further substituted as will be apparent to those having skill in the organic and medicinal chemistry arts in conjunction with the disclosure herein.

Representative substituted aminocarbonyl groups include, for example, those shown below. These can heterocyclo groups be further substituted as will be apparent to those having skill in the organic and medicinal chemistry arts in conjunction with the disclosure herein.

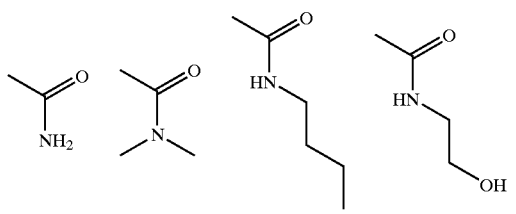

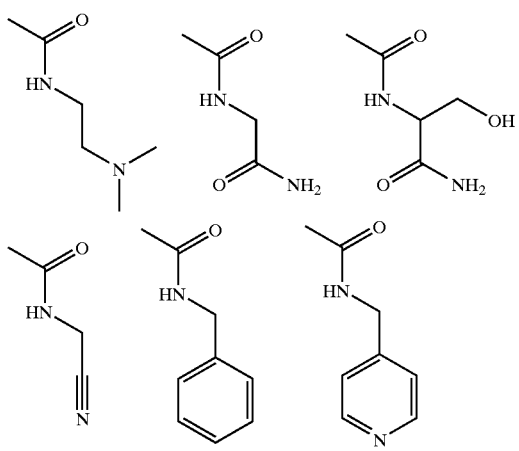

Representative substituted alkoxycarbonyl groups include, for example, those shown below. These alkoxycarbonyl groups can be further substituted as will be apparent to those having skill in the organic and medicinal chemistry arts in conjunction with the disclosure herein.

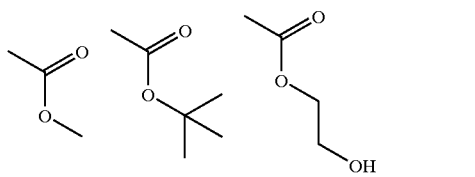

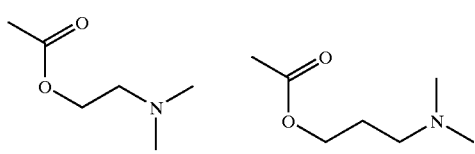

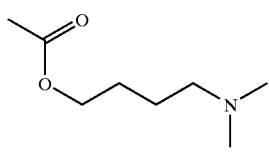

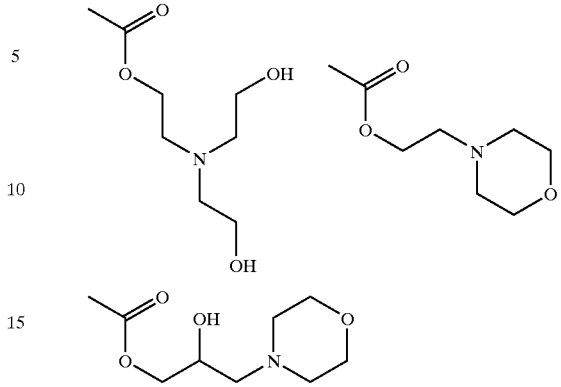

Presently preferred, representative compounds of this group include, for example, [3-(2,4-dichlorophenyl)-4-nitrophenyl]{2-[(5-nitro(2-pyridyl)amino]ethyl}amine, {2-[(6-amino-5-nitro(2-pyridyl)amino]ethyl}[3-(2,4-diclorophenyl)-4-nitrophenyl]-amine, 6-[(2-{[3-(2,4dichlorophenyl)-4-nitrophenyl]amino}ethylaminopyridine-3-carbonitrile, N-[2-(2,4dichlorophenyl)-4-({2-[(5-cyano(2-pyridyl)) amino]ethyl}-amino)phenyl]acetamide, 6-[(2-{[4-amino-3-(2,4-dichlorophenyl)phenyl]amino}-ethyl)aminopyridine-3-carbonitrile, N-[2-(2,4-dichlorophenyl)-4-({2-[(5-cyano(2-pyridyl))amino]ethyl}amino)phenyl]-2-(methylamino) acetamide, [3-(2,4-dichlorophenyl)-4-nitrophenyl]methyl{2-[(5-nitro(2-pyridyl))amino]ethyl}amine and {2-[(6-amino-5-nitro(2-pyridyl))amino]ethyl}[3-(2,4-dichlorophenyl)-4-nitrophenyl]methylamine.

In another aspect, the invention provides compositions comprising an amount of a compound of formula (I) effective to modulate GSK3 activity in a human or animal subject when administered thereto, together with a pharmaceutically acceptable carrier.

In yet other embodiments, the invention provides methods of inhibiting GSK3 activity in a human or animal subject, comprising administering to the human or animal subject a GSK3 inhibitory amount of a compound of structure (I).

The present invention further provides methods of treating human or animal subjects suffering from GSK3-mediated disorder in a human or animal subject, comprising administering to the human or animal subject a therapeutically effective amount of a compound of formula (I) above, either alone or in combination with other therapeutically active agents.

In yet other embodiments, the present invention provides compounds of formula I, as described above, for use as a pharmaceutical, as well as methods of use of those compounds in the manufacture of a medicament for the treatment of diabetes, Alzheimer's disease, other neurodegenerative disorders, such as Parkinson's disease and Huntington's disease, obesity, atherosclerotic cardiovascular disease, essential hypertension, polycystic ovary syndrome, syndrome X, ischemia, especially cerebral ischemia, traumatic brain injury, bipolar disorder, immunodeficiency or cancer.

As used above and elsewhere herein the following terms have the meanings defined below:

"Glycogen synthase kinase 3" and "GSK3" are used interchangeably herein to refer to any protein having more than 60% sequence homology to the amino acids between positions 56 and 340 of the human GSK3 beta amino acid sequence (Genbank Accession No. L33801). To determine the percent homology of two amino acid sequences or of two nucleic acids, the sequences are aligned for optimal comparison purposes (e.g., gaps can be introduced in the sequence of one polypeptide or nucleic acid for optimal alignment with the other polypeptide or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions x 100). GSK3 was originally identified by its phosphorylation of glycogen synthase as described in Woodgett et al., *Trends Biochem. Sci.*, 16:177–81. (1991), incorporated herein by reference. By modulating GSK3 kinase activity, activities downstream of GSK3 activity may be inhibited, or, alternatively, stimulated. For example, when GSK3 activity is inhibited, glycogen synthase may be activated, resulting in increased glycogen production. GSK3 is also known to act as a kinase in a variety of other contexts, including, for example, phosphorylation of c-jun, β-catenin, and tau protein. It is understood that inhibition of GSK3 kinase activity can lead to a variety of effects in a variety of biological contexts. The invention, however, is not limited by any theories of mechanism as to how the invention works.

"GSK3 inhibitor" is used herein to refer to a compound that exhibits an $IC_{50}$ with respect to GSK3 of no more than about 100 µM and more typically not more than about 50 µM, as measured in the cell-free assay for GSK3 inhibitory activity described generally hereinbelow. "$IC_{50}$" is that concentration of inhibitor which reduces the activity of an enzyme (e.g., GSK3) to half-maximal level. Representative compounds of the present invention have been discovered to exhibit inhibitory activity against GSK3. Compounds of the present invention preferably exhibit an $IC_{50}$ with respect to GSK3 of no more than about 10 µM, more preferably, no more than about 5 µM, even more preferably not more than about 1 µM, and most preferably, not more than about 200 nM, as measured in the cell-free GSK3 kinase assay.

"Optionally substituted" refers to the replacement of hydrogen with a monovalent or divalent radical. Suitable substitution groups include, for example, hydroxyl, nitro, amino, imino, cyano, halo, thio, thioamido, amidino, imidino, oxo, oxamidino, methoxamidino, imidino, guanidino, sulfonamido; carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like.

The substitution group can itself be substituted. The group substituted onto the substitution group can be carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

"Loweralkyl" as used herein refers to branched or straight chain alkyl groups comprising one to ten carbon atoms that are unsubstituted or substituted, e.g., with one or more halogen, hydroxyl or other groups, including, e.g., methyl, ethyl, propyl, isopropyl, n-butyl, t-butyl, neopentyl, trifluoromethyl, pentafluoroethyl and the like.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$-CH(CH$_3$)$_2$, —CH(CH$_3$)CH(CH$_3$)CH(CH$_3$)$_2$, —CH(CH$_2$CH$_3$)CH(CH$_3$) CH(CH$_3$)(CH$_2$-CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl, groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —CH(CH$_3$)$_2$.

"Alkylenyl" refers to a divalent straight chain or branched chain saturated aliphatic radical having from 1 to 20 carbon atoms. Typical alkylenyl groups employed in compounds of the present invention are loweralkylenyl groups that have from 1 to about 6 carbon atoms in their backbone. "Alkenyl" refers herein to straight chain, branched, or cyclic radicals having one or more double bonds and from 2 to 20 carbon atoms. "Alkynyl" refers herein to straight chain, branched, or cyclic radicals having one or more triple bonds and from 2 to 20 carbon atoms.

"Loweralkoxy" as used herein refers to RO— wherein R is loweralkyl. Representative examples of loweralkoxy groups include methoxy, ethoxy, t-butoxy, trifluoromethoxy and the like.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Halo" refers herein to a halogen radical, such as fluorine, chlorine, bromine or iodine. "Haloalkyl" refers to an alkyl radical substituted with one or more halogen atoms. The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Aryl" refers to monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic" refers herein to fused and non-fused cyclic structures in which at least one cyclic structure is aromatic, such as, for example, benzodioxozolo (which has a heterocyclic structure fused to a phenyl group, i.e.

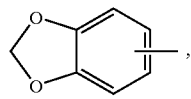

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

"Amino" refers herein to the group —NH$_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term "arylcycloalkylamino" refers herein to the group, aryl-cycloalkyl-NH—, where cycloalkyl is a divalent cycloalkyl group. Typically, cycloalkyl has from 3 to 6 backbone atoms, of which, optionally 1 to about 4 are heteroatoms. The term "aminoalkyl" refers to an alkyl group that is terminally substituted with an amino group.

The term "alkoxyalkyl" refers to the group-alk$_1$-O-alk$_2$ where alk$_1$ is alkylenyl or alkenyl, and alk$_2$ is alkyl or alkenyl. The term "loweralkoxyalkyl" refers to an alkoxyalkyl where alk$_1$ is loweralkylenyl or loweralkenyl, and alk$_2$ is loweralkyl or loweralkenyl. The term "aryloxyalkyl" refers to the group-alkylenyl-O-aryl. The term "aralkoxyalkyl" refers to the group-alkylenyl-O-aralkyl, where aralkyl is a loweraralkyl.

The term "alkoxyalkylamino" refers herein to the group —NR-(alkoxylalkyl), where R is typically hydrogen, loweraralkyl, or loweralkyl. The term "aminoloweralkoxyalkyl" refers herein to an aminoalkoxyalkyl in which the alkoxyalkyl is a loweralkoxyalkyl.

The term "aminocarbonyl" refers herein to the group —C(O)—NH$_2$. "Substituted aminocarbonyl" refers herein to the group —C(O)—NRR' where R is loweralkyl and R' is hydrogen or a loweralkyl. The term "arylaminocarbonyl" refers herein to the group —C(O)—NRR' where R is an aryl and R' is hydrogen, loweralkyl or aryl. "Aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)$_2$—NH$_2$. "Substituted aminosulfonyl" refers herein to the group —S(O)$_2$—NRR' where R is loweralkyl and R' is hydrogen or a loweralkyl. The term "aralkylaminosulfonlyaryl" refers herein to the group-aryl-S(O)$_2$—NH-aralkyl, where the aralkyl is loweraralkyl.

"Carbonyl" refers to the divalent group —C(O)—.

"Carbonyloxy" refers generally to the group —C(O)—O—. Such groups include esters, —C(O)—O—R, where R is loweralkyl, cycloalkyl, aryl, or loweraralkyl. The term "carbonyloxycycloalkyl" refers generally herein to both an "carbonyloxycarbocycloalkyl" and an "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl, where the aralkyl is loweraralkyl.

The term "sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl, in which the aralkyl is loweraralkyl. The term "sulfonamido" refers herein to —SO$_2$NH$_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—NR'—R, where R and R' are straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl.

As used herein, the term "guanidino" or "guanidyl" refers to moieties derived from guanidine, $H_2N$—C(=NH)—$NH_2$. Such moieties include those bonded at the nitrogen atom carrying the formal double bond (the "2"-position of the guanidine, e.g., diaminomethyleneamino, $(H_2N)_2$C=NH—) and those bonded at either of the nitrogen atoms carrying a formal single bond (the "1-" and/or "3"-positions of the guanidine, e.g., $H_2N$—C(=NH)—NH—). The hydrogen atoms at any of the nitrogens can be replaced with a suitable substituent, such as loweralkyl, aryl, or loweraralkyl.

As used herein, the term "amidino" refers to the moieties R—C(=N)—NR'— (the radical being at the "$N^1$" nitrogen) and R(NR')C=N— (the radical being at the "$N^2$" nitrogen), where R and R' can be hydrogen, loweralkyl, aryl, or loweraralkyl.

Compounds of the present invention can be readily synthesized using the methods described herein, or other methods, which are well known in the art.

GSK3 inhibitor compounds of the present invention can be purified using known methods, such as, for example, chromatography, crystallization, and the like.

Compounds of the present invention preferably exhibit inhibitory activity that is relatively substantially selective with respect to GSK3, as compared to at least one other type of kinase. As used herein, the term "selective" refers to a relatively greater potency for inhibition against GSK3, as compared to at least one other type of kinase. Preferably, GSK3 inhibitors of the present invention are selective with respect to GSK3, as compared to at least two other types of kinases. Kinase activity assays for kinases other than GSK3 are generally known. See e.g., Havlicek et al., *J. Med. Chem.*, 40:408–12 (1997), incorporated herein by reference. GSK3 selectivity can be quantitated according to the following: GSK3 selectivity=$IC_{50 \ (other \ kinase)} \div IC_{50 \ (GSK3)}$, where a GSK3 inhibitor is selective for GSK3 when $IC_{50 \ (other \ kinase)} > IC_{50 \ (GSK3)}$. Thus, an inhibitor that is selective for GSK3 exhibits a GSK3 selectivity of greater than 1-fold with respect to inhibition of a kinase other than GSK3. As used herein, the term "other kinase" refers to a kinase other than GSK3. Such selectivities are generally measured in the cell-free assay described in Example 20.

Typically, GSK3 inhibitors of the present invention exhibit a selectivity of at least about 2-fold (i.e., $IC_{50 \ (other \ kinase)} \div IC_{50 \ (GSK3)}$) for GSK3, as compared to another kinase and more typically they exhibit a selectivity of at least about 5-fold. Usually, GSK3 inhibitors of the present invention exhibit a selectivity for GSK3, as compared to at least one other kinase, of at least about 10-fold, desirably at least about 100-fold, and more preferably, at least about 1000-fold.

GSK3 inhibitory activity can be readily detected using the assays described herein, as well as assays generally known to those of ordinary skill in the art. Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function either by direct interaction with GSK3 itself, or by interference with GSK3 expression or with post-translational processing required to produce mature active GSK3.

In general, a cell-free GSK3 kinase assay can be readily carried out by: (1) incubating GSK3 with a peptide substrate, radiolabeled ATP (such as, for example, $\gamma^{33}P$- or $\gamma^{32}P$-ATP, both available from Amersham, Arlington Heights, Ill.), magnesium ions, and optionally, one or more candidate inhibitors; (2) incubating the mixture for a period of time to allow incorporation of radiolabeled phosphate into the peptide substrate by GSK3 activity; (3) transferring all or a portion of the enzyme reaction mix to a separate vessel, typically a microtiter well that contains a uniform amount of a capture ligand that is capable of binding to an anchor, ligand on the peptide substrate; (4) washing to remove unreacted radiolabeled ATP; then (5) quantifying the amount of $^{33}P$ or $^{32}P$ remaining in each well. This amount represents the amount of radiolabeled phosphate incorporated into the peptide substrate. Inhibition is observed as a reduction in the incorporation of radiolabeled phosphate into the peptide substrate.

Suitable peptide substrates for use in the cell free assay may be any peptide, polypeptide or synthetic peptide derivative that can be phosphorylated by GSK3 in the presence of an appropriate amount of ATP. Suitable peptide substrates may be based on portions of the sequences of various natural protein substrates of GSK3, and may also contain N-terminal or C-terminal modifications or extensions including spacer sequences and anchor ligands. Thus, the peptide substrate may reside within a larger polypeptide, or may be an isolated peptide designed for phosphorylation by GSK3.

For example, a peptide substrate can be designed based on a subsequence of the DNA binding protein CREB, such as the SGSG-linked CREB peptide sequence within the CREB DNA binding protein described in Wang et al., *Anal. Biochem.*, 220:397–402 (1994), incorporated herein by reference. In the assay reported by Wang et al., the C-terminal serine in the SXXXS motif of the CREB peptide is enzymatically prephosphorylated by cAMP-dependent protein kinase (PKA), a step which is required to render the N-terminal serine in the motif phosphorylatable by GSK3. As an alternative, a modified CREB peptide substrate can be employed which has the same SXXXS motif and which also contains an N-terminal anchor ligand, but which is synthesized with its C-terminal serine prephosphorylated (such a substrate is available commercially from Chiron Technologies PTY Ltd., Clayton, Australia). Phosphorylation of the second serine in the SXXXS motif during peptide synthesis eliminates the need to enzymatically phosphorylate that residue with PKA as a separate step, and incorporation of an anchor ligand facilitates capture of the peptide substrate after its reaction with GSK3.

Generally, a peptide substrate used for a kinase activity assay may contain one or more sites that are phosphorylatable by GSK3, and one or more other sites that are phosphorylatable by other kinases, but not by GSK3. Thus, these other sites can be prephosphorylated in order to create a motif that is phosphorylatable by GSK3. The term "prephosphorylated" refers herein to the phosphorylation of a substrate peptide with non-radiolabeled phosphate prior to conducting a kinase assay using that substrate peptide. Such prephosphorylation can conveniently be performed during synthesis of the peptide substrate.

The SGSG-linked CREB peptide can be linked to an anchor ligand, such as biotin, where the serine near the C terminus between P and Y is prephosphorylated. As used herein, the term "anchor ligand" refers to a ligand that can be attached to a peptide substrate to facilitate capture of the peptide substrate on a capture ligand, and which functions to hold the peptide substrate in place during wash steps, yet allows removal of unreacted, radiolabeled ATP. An exemplary anchor ligand is biotin. The term "capture ligand"

refers herein to a molecule which can bind an anchor ligand with high affinity, and which is attached to a solid structure. Examples of bound capture ligands include, for example, avidin- or streptavidin-coated microtiter wells or agarose beads. Beads bearing capture ligands can be further combined with a scintillant to provide a means for detecting captured radiolabeled substrate peptide, or scintillant can be added to the captured peptide in a later step.

The captured radiolabeled peptide substrate can be quantitated in a scintillation counter using known methods. The signal detected in the scintillation counter will be proportional to GSK3 activity if the enzyme reaction has been run under conditions where only a limited portion (e.g., less than 20%) of the peptide substrate is phosphorylated. If an inhibitor is present during the reaction, GSK3 activity will be reduced, and a smaller quantity of radiolabeled phosphate will thus be incorporated into the peptide substrate. Hence, a lower scintillation signal will be detected. Consequently, GSK3 inhibitory activity will be detected as a reduction in scintillation signal, as compared to that observed in a negative control where no inhibitor is present during the reaction. This assay is described in more detail in Example 265 hereinbelow.

A cell-based GSK3 kinase activity assay typically utilizes a cell that can express both GSK3 and a GSK3 substrate, such as, for example, a cell transformed with genes encoding GSK3 and its substrate, including regulatory control sequences for the expression of the genes. In carrying out the cell-based assay, the cell capable of expressing the genes is incubated in the presence of a compound of the present invention. The cell is lysed, and the proportion of the substrate in the phosphorylated form is determined, e.g., by observing its mobility relative to the unphosphorylated form on SDS PAGE or by determining the amount of substrate that is recognized by an antibody specific for the phosphorylated form of the substrate. The amount of phosphorylation of the substrate is an indication of the inhibitory activity of the compound, i.e., inhibition is detected as a decrease in phosphorylation as compared to the assay conducted with no inhibitor present. GSK3 inhibitory activity detected in a cell-based assay may be due, for example, to inhibition of the expression of GSK3 or by inhibition of the kinase activity of GSK3.

Thus, cell-based assays can also be used to specifically assay for activities that are implicated by GSK3 inhibition, such as, for example, inhibition of tau protein phosphorylation, potentiation of insulin signaling, and the like. For example, to assess the capacity of a GSK3 inhibitor to inhibit Alzheimer's-like phosphorylation of microtubule-associated protein tau, cells may be co-transfected with human GSK3β and human tau protein, then incubated with one or more candidate inhibitors. Various mammalian cell lines and expression vectors can be used for this type of assay. For instance, COS cells may be transfected with both a human GSK3β expression plasmid according to the protocol described in Stambolic et al., 1996, *Current Biology* 6:1664–68, which is incorporated herein by reference, and an expression plasmid such as pSG5 that contains human tau protein coding sequence under an early SV40 promoter. See also Goedert et al., *EMBO J.*, 8:393–399 (1989), which is incorporated herein by reference. Alzheimer's-like phosphorylation of tau can be readily detected with a specific antibody such as, for example, AT8, which is available from Polymedco Inc. (Cortlandt Manor, N.Y.) after lysing the cells. This assay is described in greater detail in the examples, hereinbelow.

Likewise, the ability of GSK3 inhibitor compounds to potentiate insulin signaling by activating glycogen synthase can be readily ascertained using a cell-based glycogen synthase activity assay. This assay employs cells that respond to insulin stimulation by increasing glycogen synthase activity, such as the CHO-HIRC cell line, which overexpresses wild-type insulin receptor (~100,000 binding sites/cell). The CHO-HIRC cell line can be generated as described in Moller et al., *J. Biol. Chem.*, 265:14979–14985 (1990) and Moller et al., *Mol. Endocrinol.*, 4:1183–1191 (1990), both of which are incorporated herein by reference. The assay can be, carried out by incubating serum-starved CHO-HIRC cells in the presence of various concentrations of compounds of the present invention in the medium, followed by cell lysis at the end of the incubation period. Glycogen synthase activity can be detected in the lysate as described in Thomas et al., *Anal. Biochem.*, 25:486–499. (1968). Glycogen synthase activity is computed for each sample as a percentage of maximal glycogen synthase activity, as described in Thomas et al., supra, and is plotted as a function of candidate GSK3 inhibitor concentration. The concentration of candidate GSK3 inhibitor that increased glycogen synthase activity to half of its maximal level (i.e., the $EC_{50}$) can be calculated by fitting a four parameter sigmoidal curve using routine curve fitting methods that are well known to those having ordinary skill in the art. This is described in more detail in Example 266, hereinbelow.

GSK3 inhibitors can be readily screened for in vivo activity such as, for example, using methods that are well known to those having ordinary skill in the art. For example, candidate compounds having potential therapeutic activity in the treatment of type 2 diabetes can be readily identified by detecting a capacity to improve glucose tolerance in animal models of type 2 diabetes. Specifically, the candidate compound can be dosed using any of several routes prior to administration of a glucose bolus in either diabetic mice (e.g. KK, db/db, ob/ob) or diabetic rats (e.g. Zucker Fa/Fa or GK). Following administration of the candidate compound and glucose, blood samples are removed at preselected time intervals and evaluated for serum glucose and insulin levels. Improved disposal of glucose in the absence of elevated secretion levels of endogenous insulin can be considered as insulin sensitization and can be indicative of compound efficacy. A detailed description of this assay is provided in the examples, hereinbelow.

Similarly, GSK3 inhibitors can be readily screened for neuroprotective activity such as, for example, using methods that are well known to those having ordinary skill in the art. For example, candidate compounds having potential neuroprotective activity can be readily identified by the middle cerebral artery occlusion model of Maier et al. (Maier, C. M. et al, "Optimal depth and duration of mild hypothermia in a focal model of transient cerebral ischemia" *Stroke* 29:2171–2180 (1998)). In this model, Adult male rats are anesthetized. The right femoral artery is catheterized for monitoring blood pressure, collecting blood samples, and infusion of saline and introduction of experimental compounds. A stroke is produced by inserting a monofilament suture to occlude the middle cerebral artery. The suture is kept in place for 2 hours. After suture removal, the tissue is reperfused for 22–72 hours. Compounds can be administered before, during, or after onset of ischemia. Following the 24–72 hour survival animals are euthanized and the brains quickly removed and sectioned. Brain sections are processed for tetrazolium chloride, hematoxylin and eosin, cresyl violet and immuno-histology. The area of infarct is determined by light microscopy and expressed as a percentage of total left hemisphere area. Preferred GSK3 inhibitors of the invention reduce the size of infarct in the MCAO model.

GSK3 inhibitors of the invention are readily screened for anti-Parkinson's activity using the methylphenyltetrahydropyridine (MPTP) model of Mandir et al. (Mandir, A. S. et al., "Poly(ADP-ribose) polymerase activation mediates 1-methyl-4-phenyl-1,2,3,6-tetrahydropyridine (MPTP)-induced parkinsonism," P.N.A.S. 96(10):5774–5779 (1999)). Parkinson's disease is a progressive disorder characterized by the selective degeneration of neurons in the substantia nigra. In vivo, MPTP, which is converted to the active metabolite MPP+, causes subacute Parkinsonism in primates and destruction of substantia nigra neurons in rodents. To assess compounds that may disrupt or slow the progression of this disease the MPTP rodent model is used. Adult rats or mice are given 2–4 i.p. injections of MPTP 2–12 hours apart (30 mg/kg), causing destruction of the dopaminergic nigostriatal pathway. GSK3 inhibitors are continuously administered i.v. via an osmotic minipump for 7 days. Animals are euthanized and the brains removed. Brain areas are analyzed for the presence of tyrosine hydroxylase fibers, apoptotic cells, and dopamine. Preferred GSK3 inhibitors of the invention demonstrate increased survival of neurons and fibers in the substantia nigra.

GSK3 inhibitors of the invention are readily screened for anti-Huntington's activity using the quinolinic acid lesion model of Anderson et al. (Anderson, K. D. et al., "Ciliary neurotrophic factor protects striatal output neurons in an animal model of Huntington disease," P.N.A.S. 93:7346–7351 (1996)). In this model system, adult rats are given unilateral striatal injections of quinolinic acid. This causes marked cell loss in the striatum 7 days later. Treatment with GSK3 inhibitors at the time of QA injection and during the 7-day recovery period should inhibit the QA induces striatal damage as evaluated histologically.

Activity of the GSK3 inhibitors of the invention may also be assessed using the motor neuron degeneration model of Alberi et al., (Alberi, S. et al., "Axotomized neonatal motoneurons overexpressing the bcl2 proto-oncogene retain functional electrophysiological properties," P.N.A.S. 93:3978–3983 (1996)). In this model, unilateral axotomy of the facial nerve in 2–4 day old rats results in death of 40–90% of motor neurons in the facial nucleus. GSK3 inhibitors will be introduced at the site of the lesion in a gelfoam sponge or by injection. Seven to 10 days following lesioning the animals are euthanized and the motor neurons of the facial nucleus are stained (cresyl violet) and counted. Preferred GSK3 inhibitors of the invention protect facial neurons from lesion-induced death.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerolphosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, sulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethyl amine, trimethylamine, triethylamine, ethylamine, and the like. Other representative organic amines useful for the formation of base addition salts include diethylamine, ethylenediamine, ethanolamine, diethanolamine, piperazine and the like.

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, and the like.

In accordance with other embodiments of the present invention, there is provided a composition comprising GSK3-inhibitor compound of the present invention, together with a pharmaceutically acceptable carrier or excipient.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey. (1991), incorporated herein by reference.

Pharmaceutical compositions containing GSK-3 inhibitor compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

In accordance with yet other embodiments, the present invention provides methods for inhibiting GSK3 activity in a human or animal subject, said method comprising administering to a subject an amount of a GSK3 inhibitor compound having the structure (I), or composition comprising such compound, effective to inhibit GSK3 activity in the subject. Other embodiments provided methods for treating a cell or a GSK3-mediated disorder in a human or animal subject, comprising administering to the cell or to the human or animal subject an amount of a compound or composition of the invention effective to inhibit GSK3 activity in the cell or subject. Preferably, the subject will be a human or non-human animal subject. Inhibition of GSK3 activity includes detectable suppression of GSK3 activity either as compared to a control or as compared to expected GSK3 activity.

Effective amounts of the compounds of the invention generally include any amount sufficient to detectably inhibit GSK3 activity by any of the assays described herein, by other GSK3 kinase activity assays known to those having ordinary skill in the art or by detecting an alleviation of symptoms in a subject afflicted with a GSK3-mediated disorder.

GSK3-mediated disorders that may be treated in accordance with the invention include any biological or medical disorder in which GSK3 activity is implicated or in which the inhibition of GSK3 potentiates signaling through a pathway that is characteristically defective in the disease to be treated. The condition or disorder may either be caused or characterized by abnormal GSK3 activity.

Represeantative GSK3-mediated disorders include, for example, type 2 diabetes, Alzheimer's disease, other neurodegenerative disorders, such as Parkinson's disease and Huntington's disease, obesity, atherosclerotic cardiovascular disease, essential hypertension, polycystic ovary syndrome, syndrome X, ischemia, especially cerebral ischemia, traumatic brain injury, bipolar disorder, immunodeficiency, cancer and the like.

Successful treatment of a subject in accordance with the invention may result in the inducement of a reduction or alleviation of symptoms in a subject afflicted with a medical or biological disorder to, for example, halt the further, progression of the disorder, or the prevention of the disorder. Thus, for example, treatment of diabetes can result in a reduction in glucose or HbA1c levels in the patient. Likewise, treatment of Alzheimer's disease can result in a reduction in rate of disease progression, detected, for example, by measuring a reduction in the rate of increase of dementia.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be from about 0.1 mg/kg/day to about 100 mg/kg/day, preferably from about 1 mg/kg/day to about 20 mg/kg/day, and most preferably from about 2 mg/kg/day to about 10 mg/kg/day of a GSK3 inhibitor compound of the present invention, which may be administered in one or multiple doses.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example Prescott, Ed., *Methods in Cell Biology*, Volume XIV, Academic Press, New York, N.W., p. 33 et seq (1976).

While the compounds of the invention can be administered as the sole active pharmaceutical agent, they can also be used in combination with one or more other agents used in the treatment of disorders. Representative agents useful in combination with the compounds of the invention for the treatment of type 2 diabetes include, for example, insulin, troglitazone, rosiglitazone, pioglitazone, glipizide, metformin, acarbose, and the like. Representative agents useful in combination with the compounds of the invention for the treatment of Alzheimer's disease include, for example, donepezil, tacrine and the like. Representative agents useful in combination with the compounds of the invention for the treatment of bipolar disease include, for example, lithium salts, valproate, carbamazepine and the like. A representative agent useful in combination with the compounds of the invention for the treatment of stroke is, for example, tissue plasminogen activator.

When additional active agents are used in combination with the compounds of the present invention, the additional active agents may generally be employed in therapeutic amounts as indicated in the PHYSICIANS' DESK REFERENCE (PDR) 53$^{rd}$ Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The foregoing may be better understood by reference to the following examples, which are presented for illustration and not to limit the scope of the inventive concepts.

EXAMPLES

Example 1

Characterization and Purification Methods

Compounds of the present invention were characterized by high performance liquid chromatography (HPLC) using a Waters Millennium chromatography system with a 2690 Separation Module (Milford, Mass.). The analytical columns were Column Engineering 5μ Reliasil C18 column (50×4.6 mm), with gradient ramping from 5% to 80% acetonitrile in water in 18 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass- or plastic-backed silica gel plates, such as, for example, Baker-Flex Silica Gel 1 B2-F flexible sheets. TLC results were readily detected visually under ultraviolet light, or by employing well known iodine vapor and other various staining techniques.

Mass spectrometric analysis was performed on a Fisons VG Electrospray Mass Spectrometer. All masses are reported as those of the protonated parent ions.

Nuclear magnetic resonance (NMR) analysis was performed with a Varian 300 MHz NMR (Palo Alto, Calif.). The spectral reference was either TMS or the known chemical shift of the solvent. Some compound samples were run at elevated temperatures (i.e., 75° C.) to promote increased sample solubility.

The purity of some of the invention compounds was assessed by elemental analysis (Desert Analytics, Tucson, Ariz.)

Melting points were determined on a Laboratory Devices Mel-Temp apparatus (Holliston, Mass.).

Example 2

Synthesis of 2-(2,4-dichlorophenyl)-4-fluoro-1-nitrobenzene

The mixture containing 1-bromo 5-fluoro 2-nitrobenzene (1 g, 4.5 mmol), 2,4-dichloro benzeneboronicacid (907 mg, 4.7 mmol), sodiumcarbonate (1.44 g, 13.5 mmol) in benzene and 3 ml of water was purged with nitrogen for 30 mins. Tetrakis(triphenylphosphine)-palladium(0) (264 mgs, 0.2 mmol) was added to the mixture and was heated to 75° C. overnight. The reaction mixture was partitioned between ethyl acetate and water. Organic layer was separated and washed with brine, dried (MgSO$_4$), filtered and concentrated in vacuo to give a brown solid which was recrystallized to give 1 g (yield, 80%) of white solid. The product gave satisfactory NMR.

HPLC: 13.2 min (100%)

MS (M+H/Z), 266

Example 3

Synthesis of N-(2',4'-dichloro-6-nitro-1,1'-biphenyl-3-yl)-N'-(5-nitropyridin-2-yl)ethane-1,2-diamine

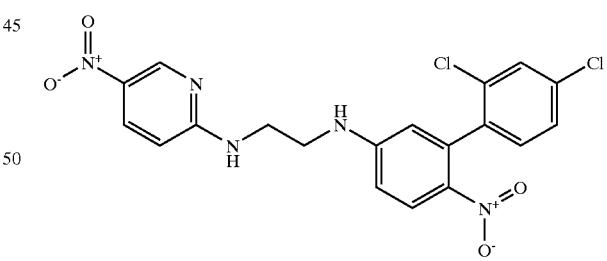

To 2-(2,4-dichlorophenyl)-4-fluoro-1-nitrobenzene (30 mgs, 0.1 mmol) in acetonitrile was added 2-(2-aminoethylamino)-5-niropyridine (19 mgs,0.1 mmol) and N,N-diisopropylethyl amine(18 μl, 0.1 mmol), and the mixture was heated to 80° C. over-night. The mixture was partitioned between ethyl acetate and water and organic layer was dried (MgSO$_4$) and concentrated. Purification on silica gel with 5% methanol in dichloromethane as eluent yielded 32 mgs of N-(2',4'-dichloro-6-nitro-1,1'-biphenyl-3-yl)-N'-(5-nitropyridin-2-yl)ethane-1,2-diamine.

HPLC: 12.6 min (90%)

MS (M+H/Z), 448

Example 4

Synthesis of N~6~-{2-[(2',4'-dichloro-6-nitro-1,1'-biphenyl-3-yl)amino]ethyl}-2,6-diamine

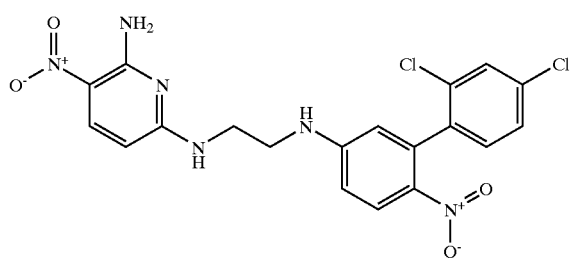

To 2-(2,4-dichlorophenyl)-4-fluoro-1-nitrobenzene (20 mgs, 0.06 mmol) in N,N-dimethylformamide was added 2-amino-3-nitro-6-(2-aminoethylamino)pyridine (14 mgs, 0.07 mmol) and N,N-diisopropylethyl amine (16 μl, 0.07 mmol) and heated to 80° C. over-night. The mixture was partitioned between ethyl acetate and water and the organic layer was dried (MgSO₄) and concentrated. Purification on silica gel with 5% methanol in dichloromethane as eluent yielded 7 mgs of N~6~-{2-[(2',4'-dichloro-6-nitro-1,1'-biphenyl-3-yl)amino] ethyl}-3-nitropyridine-2,6-diamine.

HPLC: 11.5 min(100%)

MS (M+H/Z), 463

Example 5

Synthesis of 6-({2-[(2',4'-dichloro-6-nitro-1,1'-biphenyl-3-yl)amino]ethyl}amino)nicotinonitrile

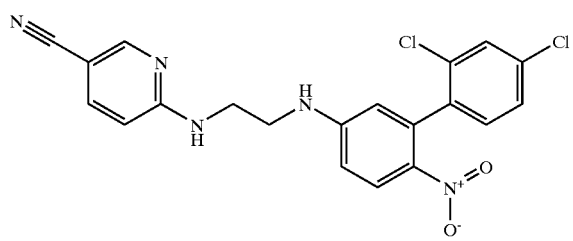

To 2-(2,4-dichlorophenyl)-4-fluoro-1-nitrobenzene(32 mgs, 0.1 mmol) in acetonitrile was added 2-(2-aminoethylamino)-5-cyanopyridine (19.2 mgs, 0.1 mmol) and N,N diisopropylethylamine (18 μl, 0.1 mmol), and the mixture was heated to 85° C. over-night. The mixture was partitioned between ethyl acetate and water and the organic layer was dried (MgSO₄) and concentrated. Purification on silica gel with 5% methanol in dichloromethane as the eluent yielded 25 mgs of 6-({2-[(2',4'-dichloro-6-nitro-1,1'-biphenyl-3-yl)amino]ethyl}amino)nicotinonitrile.

HPLC: 13.1 min (90%)

MS (M+H/Z), 428

Example 6

Synthesis of N-[2',4'-dichloro-5-({2-[(5-cyanopyridin-2-yl)amino]ethyl}amino)-1,1'-biphenyl-2-yl]acetamide

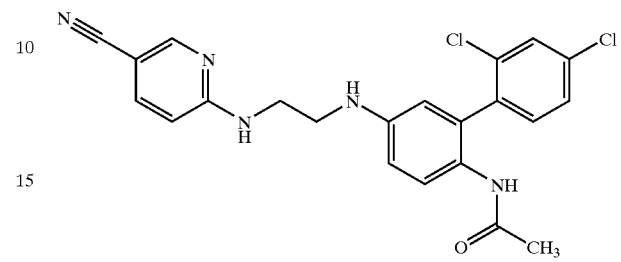

To 6-[(2-{[3-(2,4dichlorophenyl)-4-nitrophenyl]amino}ethylaminopyridine-3-carbonitrile (40 mgs, 0.1 mmol) in dichloromethane was added 50 μl of trifluoroacetic anhydride, and the mixture was stirred for 10 mins. The solution was concentrated and to it was added SnCl₂ (90 mgs, 0.5 mmol) and 2 mls of a solution of 100 μl hydrochloric acid in (1:4) dioxane:H₂O. The solution was stirred for 1 h. The mixture was partitioned between ethyl acetate and water and 44 mgs of N-[4-amino-3-(2,4-dichlorophenyl)phenyl]-N-{2-[(5-cyano(2-pyridyl))amino]ethyl}-2,2,2-trifluroacetamide was isolated. To it in dichloromethane added 10 μl of acetyl chloride and 13 μl of N,N-diisopropylethylamine and in 30 mins the acetylated product is seen on LC/MS. After an aqueous work up, to the product in (1:1) water:dioxane added 10 mgs K₂CO₃ and stirred for 2 h. The mixture was partitioned between ethyl acetate and water and the organic layer was dried (MgSO₄) and on tituration with ether yielded 20 mgs of N-[2',4'-dichloro-5-({2-[(5-cyanopyridin-2-yl)amino]ethyl}amino)-1,1'-biphenyl-2-yl]acetamide.

HPLC: 7.2 mins (99%)

MS (M+H/Z), 440

Example 7

Synthesis of 6-({2-[(6-amino-2',4'-dichloro-1,1'-biphenyl-3-yl)amino]ethyl}amino)nicotinonitrile

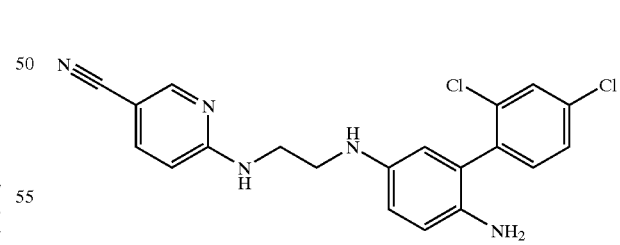

To 40 mgs of 6-[(2-{[3-(2,4dichlorophenyl)-4-nitrophenyl]amino}ethyl-aminopyridine-3-carbonitrile in ethyl alcohol with catalytic amounts of 10% Pd/C was added 500 μl of hydrazine and the solution refluxed for 2 h. The catalyst was filtered off and the filtrate was concentrated in vacuo to yield 22 mgs of 6-({2-[(6-amino-2',4'-dichloro-1,1'-biphenyl-3-yl)amino]ethyl}amino)nicotinonitrile.

HPLC: 6.7 min (80%)

MS (M+H/Z), 398

Example 8

Synthesis of N~1~-[2',4'-dichloro-5-({2-[(5-cyan-opyridin-2-yl)amino]ethyl}amino)-1,1'-biphenyl-2-yl]-N~2~-methylglycinamide

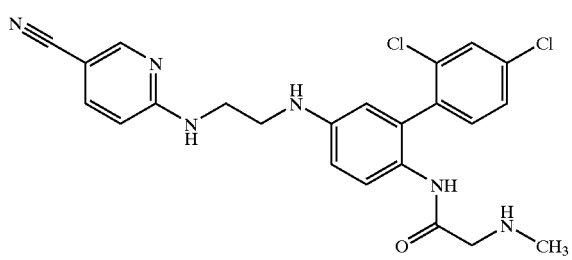

To 20 mgs of 6-[(2-{[4-amino-3-(2,4-dichlorophenyl)phenyl]amino}ethyl)-aminopyridine-3-carbonitrile in tetrahydrofuran was added 19 mgs of BOC-sarcosine, 38 mgs of HBTU and 26.2 µl of N,N-diisopropylethylamine, and the mixture was stirred at room temperature over-night. After partitioning the mixture between ethyl acetate and water the organic layer was concentrated. To it was added dichloromethane and TFA to yield 1.2 mgs of 93% pure N~1~-[2',4'-dichloro-5-({2-[(5-cyanopyridin-2-yl)amino]ethyl}amino)-1,1'-biphenyl-2-yl]-N~2~-methylglycinamide as the TFA salt after HPLC purification.

MS: (M+H/Z), 469

Example 9

Synthesis of N-(2',4'-dichloro-6-nitro-1,1'-biphenyl-3-yl)-N-methyl-N'-(5-nitropyridin-2-yl)ethane-1,2-diamine

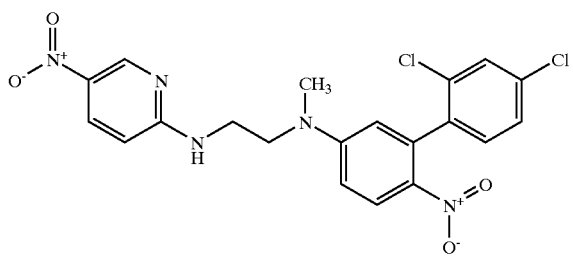

To 22 mgs of 2-(2,4-dichlorophenyl)-4-fluoro-1-nitrobenzene in N,N-dimethylformamide was added 1–5 mgs of [2-(methylaminoethyl)(5-nitro(2-pyridyl))-amine and 30 µl of N,N-diisopropylethylamine, and the mixture was heated to 85° C. over-night. After partitioning the mixture between ethyl acetate and water the organic layer was concentrated and dried (MgSO₄) and recrystallized to yield 6 mgs of N-(2',4'-dichloro-6-nitro-1,1'-biphenyl-3-yl)-N-methyl-N'-(5-nitropyridin-2-yl)ethane-1,2-diamine.

HPLC: 13.2 min (100%)
MS: MS (M+H/Z), 462

Example 10

Synthesis of N~6~-{2-[(2',4'-dichloro-6-nitro-1,1'-biphenyl-3-yl)(methyl)amino]ethyl}-3-nitropyridine-2,6-diamine

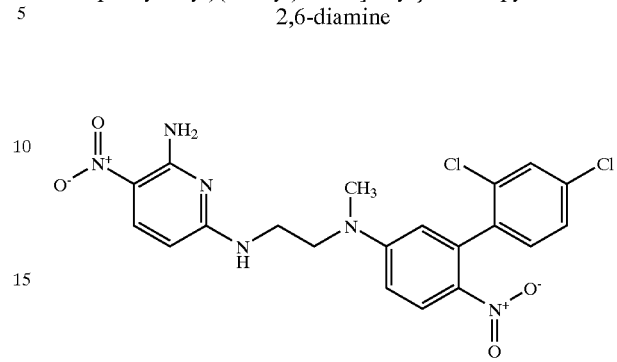

To 10 mgs of 2-(2,4-dichlorophenyl)-4-fluoro-1-nitrobenzene in acetonitrile was added 10 mgs of (6-amino-5-nitro(2-pyridyl))[2-(methylamino)ethyl]amine and 7 µl of N,N-diisopropylethylamine, and the mixture was heated to 85° C. over-night. After an aqueous work up the crude was purified on a silica gel column with 30% acetone in hexane as the eluent to give 6 mgs of N~6~-{2-[(2',4'-dichloro-6-nitro-1,1'-biphenyl-3-yl)(methyl)amino]ethyl}-3-nitropyridine-2,6-diamine.

HPLC, 12.1 min (85%)
MS (M+H/Z), 477

Example 11

Synthesis of 1-[5-({2-[(6-amino-5-nitropyridin-2-yl)amino]ethyl}amino)-2',4'-dichloro-1,1'-biphenyl-2-yl]-4-methylpiperazin-2-one

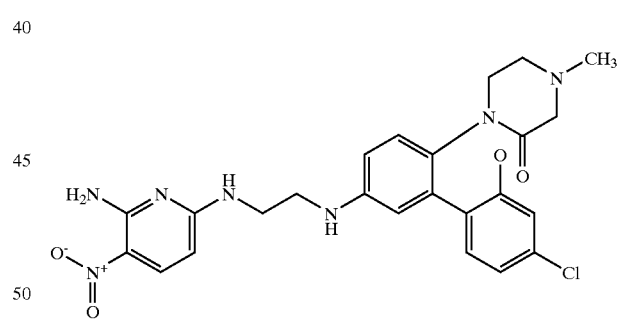

A. Preparation of N-[4-({2-[(6-amino-5-nitro(2-pyridyl))amino]ethyl}amino)-2-(2,4-dichlorophenyl)phenyl]-2-bromoacetamide Aqueous NaHCO₃ (8 eq) was added to the stirred solution of [4-amino-3-(2,4-dichlorophenyl)phenyl]{2-[(6-amino-5-nitro(2-pyridyl))amino]ethyl}amine (1 eq) in EtOAc at room temperature. 2-bromoacetyl chloride (1.5 eq) in minimal EtOAc was added slowly to the vigorously stirred reaction solution. The reaction was monitored by LC/MS and determined to be complete within 30 min. The organic layer was separated and washed with water, brine, dried (Na₂SO₄), filtered, and concentrated to dryness to give the crude N-[4-({2-[(6-amino-5-nitro(2-pyridyl))amino]ethyl}amino)-2-(2,4-dichlorophenyl)phenyl]-2-bromoacetamide as a dark yellow glass in 76% yield (~90% pure, LC/MS m/z 555.2 MH+). The product was stored at −4° C. to avoid decomposition.

B. Preparation of N-[4-({2-[(6-amino-5-nitro(2-pyridyl))amino]ethyl}amino)-2-(2,4-dichlorophenyl)phenyl]-2-[(2-hydroxyethyl)methylamino]acetamide N-Methyl ethanolamine (2 eq) was added to a stirred solution N-[4-({2-[(6-amino-5-nitro(2-pyridyl))amino]ethyl}amino)-2-(2,4-dichlorophenyl)phenyl]-2-bromoacetamide (8.65 eq) in CH$_3$CN at room temperature. The reaction was monitored by LC/MS and was determined to be complete after 12 hours. The reaction was concentrated and purified by silica column chromatography eluting with MeOH in CH$_2$Cl$_2$ (5:95, v/v). After collecting the purified fractions and concentrating, N-[4-({2-[(6-amino-5-nitro(2-pyridyl))amino]ethyl}amino)-2-(2,4-dichlorophenyl)phenyl]-2-[(2-hydroxyethyl)methylamino]acetamide was obtained as a light yellow glass (21% yield, LC/MS m/z 549.4 MH+) in 95% purity.

C. Preparation of 1-[5-({2-[(6-amino-5-nitropyridin-2-yl)amino]ethyl}amino)-2',4'-dichloro-1,1'-biphenyl-2-yl]-4-methylpiperazin-2-one DEAD (2.5 eq) and PPh$_3$ (2 eq) were added to N-[4-({2-[(6-amino-5-nitro(2-pyridyl))amino]ethyl}amino)-2-(2,4-dichlorophenyl)phenyl]-2-[(2-hydroxyethyl)-methylamino]acetamide (1 eq) dissolved in THF at room temperature. The reaction was heated to 55° C. for 1 hour until completion was determined by LC/MS. The reaction was concentrated and purified by silica column chromatography, eluting with MeOH in CH$_2$Cl$_2$ (5:95, v/v). After collecting the purified fractions and concentrating, 1-[5-({2-[(6-amino-5-nitropyridin-2-yl)amino]ethyl}amino)-2',4'-dichloro-1,1'-biphenyl-2-yl]-4-methylpiperazin-2-one was attained as a light yellow glass (LC/MS m/z 531.4 MH+) in quantitative yields.

Examples 12–15

Following the general procedures set forth herein, the following additional compounds were synthesized:

| Example | Structure | Name | MH+ |
|---|---|---|---|
| 12 | 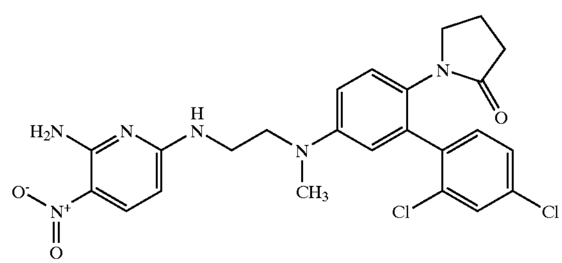 | 1-{5-[{2-[(6-amino-5-nitropyridin-2-yl)amino]ethyl}(methyl)amino]-2',4'-dichloro-1,1'-biphenyl-2-yl}-pyrrolidin-2-one | 515 |
| 13 | 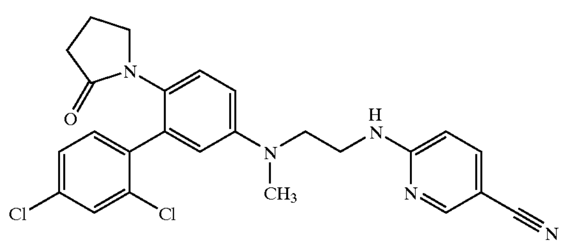 | 6-({2-[[2',4'-dichloro-6-(2-oxo-pyrrolidin-1-yl)-1,1'-biphenyl-3-yl](methyl)amino]ethyl}amino)-nicotinonitrile | 480 |
| 14 | 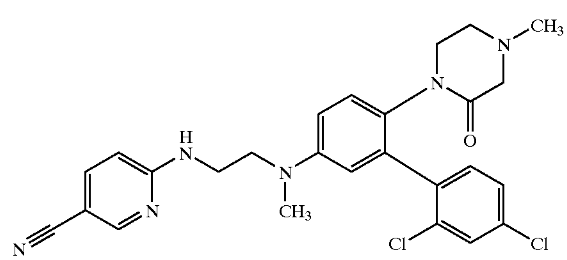 | 6-({2-[[2',4'-dichloro-6-(4-methyl-2-oxopiperazin-1-yl)-1,1'-biphenyl-3-yl](methyl)amino]ethyl}amino)nicotinonitrile | 509 |
| 15 | 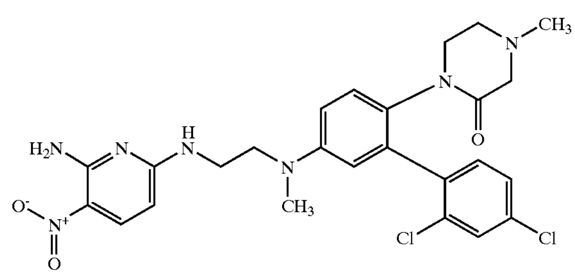 | 1-{5-[{2-[(6-amino-5-nitropyridin-2-yl)amino]ethyl}(methyl)amino]-2',4'-dichloro-1,1'-biphenyl-2-yl}-4-methylpiperazin-2-one | 544 |

Example 16

Synthesis of Acid and Alkyl Carbocycle Analogues

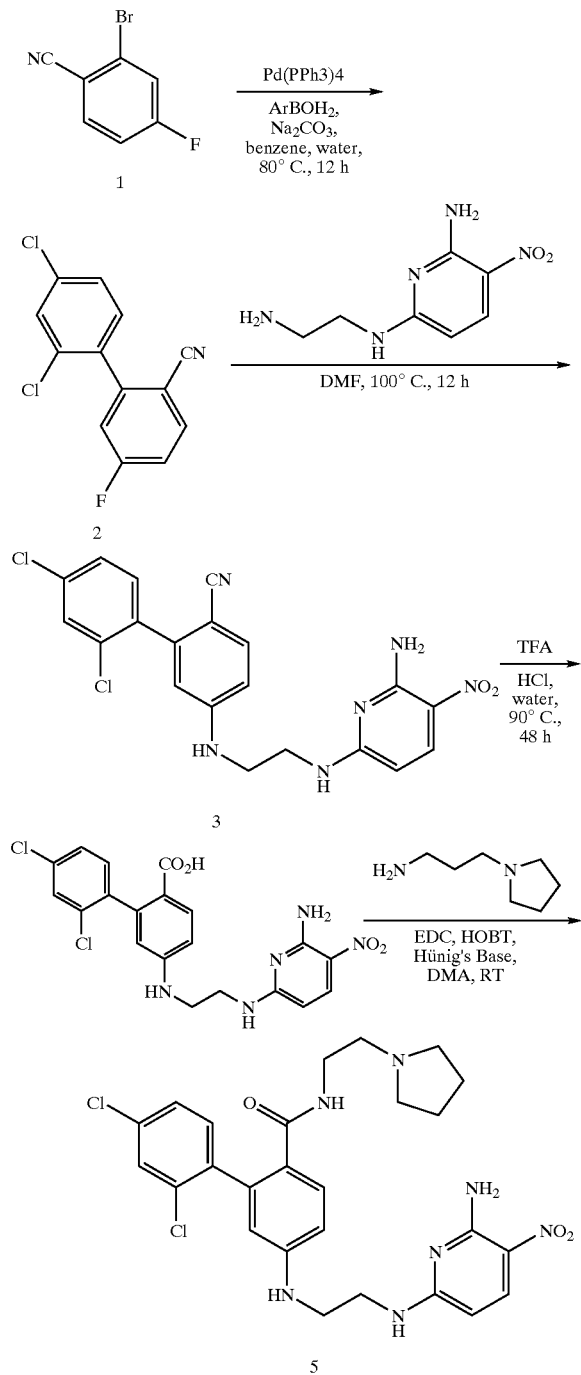

Preparation of 2-bromo-4-fluorobenzenecarbonitrile (1).

The starting material 2-bromo-4-fluorobenzenecarbonitrile (1) is purchased from Esprix Technologies of Sarasota Fla. It may alternatively be prepared by the method of Engelhardt, E. L.; Christy, M. E. Division of U.S. Pat. No. 3,812,177, 1976; U.S. Pat. Nos. 3,978,127.

Preparation of 2-(2,4-dichlorophenyl)-4-fluorobenzenecarbonitrile (2).

This material may be prepared by the Suzuki method for Example 2 in the application—see 2-(2,4-dichlorophenyl)-4-fluoro-1-nitrobenzene.

Preparation of 4-({2-[(6-amino-5-nitro(2-pyridyl))amino]ethyl}amino)-2-(2,4-dichlorophenyl)benzenecarbonitrile (3).

This material may be prepared by the aromatic displacement method for Example 3 in the application—see [3-(2,4-dichlorophenyl)-4-nitrophenyl]{2-[(5-nitro(2-pyridyl)amino]ethyl}amine, except that higher temperatures (90–120° C.) and longer reactions times (12–48 h) are needed. Also, the reactions are purged of oxygen and run under argon atmosphere. After extractions with water (2×), sat. aq. $Na_2CO_3$ (3×) and brine (1×), the reaction is dried with $Na_2SO_4$.

The starting material (2-aminoethyl)(6-amino-5-nitro(2-pyridyl))amine is prepared in the following manner. A mixture of 2-amino-6-chloro-3-nitropyridine (65 g, 376 mmol), acetonitrile (400 ml), and ethylene diamine (500 ml) are stirred overnight (ca. 20 h) at 75–80° C. under argon. When the diamine is added, this reaction can become exothermic! The ethylene diamine is removed under reduced pressure, and then in vacuo (12 h). The completely dried material is suspended in 2M sodium hydroxide solution (500 ml) with vigorous stirring for 30 min. The solid is filtered. The yellow solid is suspended in water (500 ml) with vigorous stirring for 30 min., after which the solid is filtered. The water wash and filtration is repeated one more time to get rid of salts. The yellow solid is dried in vacuo. The crude yellow solid is triturated with ether (3×500 ml) and dried overnight in vacuo resulting in 59 g of 2-(2-aminoethyl)amino-6-amino-5-nitropyridine in >99% purity.

Preparation of 4-({2-[(6-amino-5-nitro(2-pyridyl))amino]ethyl}amino)-2-(2,4-dichlorophenyl)benzoic Acid (4).

Water (5 ml) and TFA (15 ml) are added to benzonitrile (3) (100 mg, 0.2 mmol) at room temperature with stirring to form a solution. To the stirred yellow solution, con. HCl (10 ml) is added under $N_2$. The reaction is heated to 90° C. for about 2 days until complete by LCMS. The reaction is lyophilized to dryness giving the carboxylic acid (4) as the TFA salt. The product 4 is obtained as a yellow powder in 85% purity by HPLC and LCMS. The mass recovery is nearly quantitative. The product is used with out further purification.

Preparation of [4-({2-[(6-amino-5-nitro(2-pyridyl))amino]ethyl}amino)-2-(2,4-dichlorophenyl)phenyl]-N-(2-pyrrolidinylethyl)carboxamide (5).

The amine (1.5–2.0 equivalents) is added to a stirred solution of acid 4 (1.0 eq., 25 mg), HBTU (1.5 eq.), Hünig's base (2.0 eq.) and DMF (0.4 ml). The acid 4 is pre-activated by premixed the acid 4, HBTU, Hünig's base and DMF together sequentially in this order in a vial at room temperature under argon. The reaction is stirred for 3–4 h until complete as shown by LCMS and HPLC. At times, it is necessary to add 0.25 or 0.5 equivalents more of the coupling reagents to complete the reaction. The reaction is purified by preparative HPLC. The entire reaction is injected directly onto the preparative HPLC. The purified fractions are pooled and lyophilized to give the amide 5 as a yellow powder in greater than 85% purity and in yields of 50–70%.

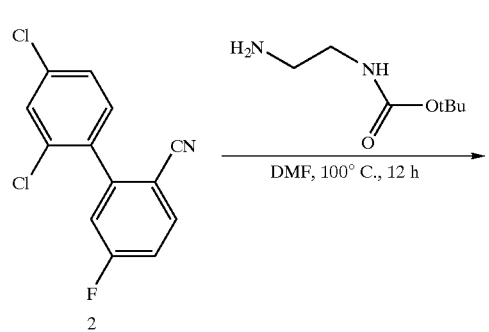
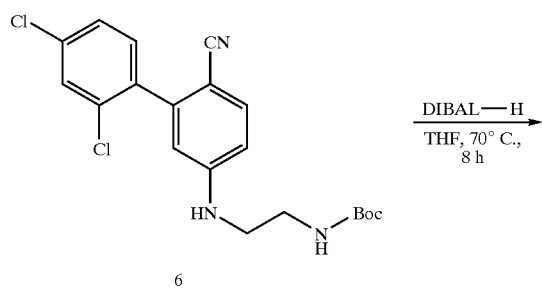
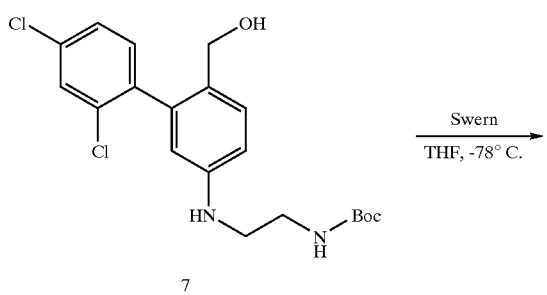
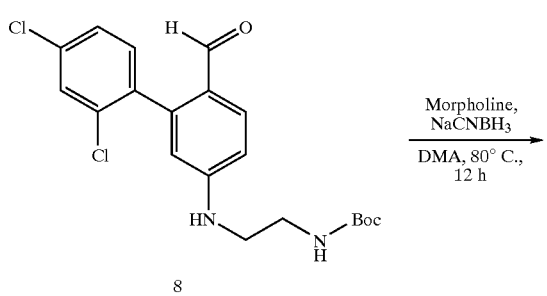
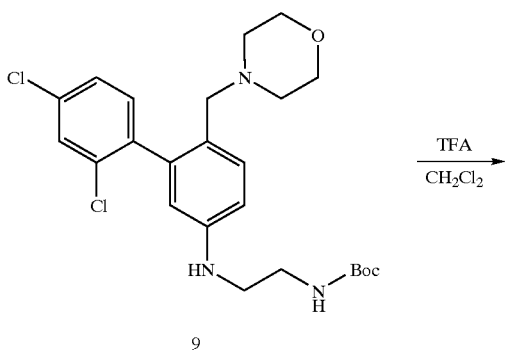
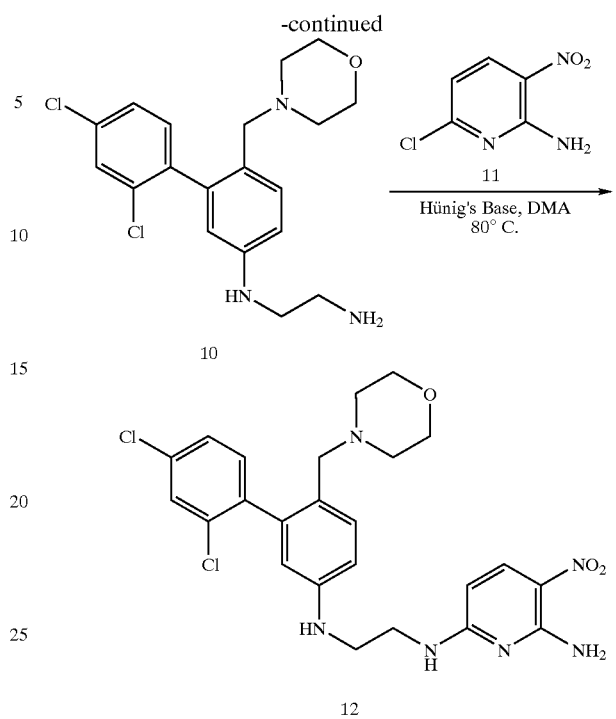

Preparation of N-(2-{[3-(2,4-dichlorophenyl)-4-cyanophenyl]amino}ethyl)(tert-butoxy)carboxamide (6).

This material is prepared by heating the slurry in DMF at 100 C for 12 h. Excess Boc-ethylenediamine may be used to drive the reaction to completion. (See example 4).

Preparation of N-(2-{[3-(2,4-dichlorophenyl)-4-(hydroxymethyl)phenyl]amino}-ethyl)(tert-butoxy)carboxamide (7).

To a stirred solution of N-(2-{[3-(2,4-dichlorophenyl)-4-cyanophenyl]-amino}ethyl)(tert-butoxy)carboxamide (2.13 g) in THF (10 ml) at room temperature under nitrogen is added of DIBAL-H (5 equiv.) (1 M in THF) dropwise. After 1 h the resulting solution is heated to 70° C. for an additional 7 h. The reaction is then cooled and quenched by the addition of Rochelle's salt. The resulting suspension is partitioned between methylene chloride (120 ml) and water (30 ml). The aqueous layer is extracted twice with methylene chloride (25 ml) and the combined organic layers washed with brine (30 ml) and dried with sodium sulfate. Concentration gives 2.05 g of a yellow foam. Chromatography on silica gel (110 g) using methanol/EtOAc as eluent gives ~20% yield of product 7.

Preparation of N-(2-{[3-(2,4-dichlorophenyl)-4-carbonylphenyl]amino}ethyl)(tert-butoxy)carboxamide (8).

Using the method of Swern, et al., N-(2-{[3-(2,4-dichlorophenyl)-4-(hydroxymethyl)phenyl]amino}ethyl)(tert-butoxy)carboxamide (100 mg) is dissolved in anhydrous methylene chloride (1 ml) and added to a premixed solution of oxalyl chloride (1.5 eq) and DMSO (3 eq) in methylene chloride (25 ml) which has been stirring at −78° C. for 15 min. The resulting solution is stirred at −78° C. for an additional 30 min, at which time triethyl amine (6 eq) is added. The resulting suspension is allowed to warm to room temperature. After 15 min., water (1 ml) is added and the layers separated. The aqueous layer is extracted with methylene chloride (2×10 ml), and the combined organic layers dried (sodium sulfate) and concentrated to afford aldehyde 8 in 70–80% yield as a light yellow foam. This product proves to be unstable and is used without further manipulation.

Preparation of N-(2-{[3-(2,4-dichlorophenyl)-4-(morpholin-4-ylmethyl)phenyl]-amino}ethyl)(tert-butoxy)carboxamide (9).

Sodium cyanoborohydride (2eq). (1M in THF) is added to a solution of aldehyde 8 (50 mg, 0.121 mmol), morpholine (2eq) and glacial acetic acid (5 ml) dissolved in THF (5 ml) at room temperature with stirring. The mixture is heated to 70° C. for 18 h, after which, a slow addition of water (1 ml) is used to decompose excess reagent. The mixture is partitioned between ethyl acetate (30 ml) and saturated citric acid solution (10 ml). The organic layer is discarded, and the aqueous layer is carefully basified with 1M aq. sodium hydroxide to pH 9. Then the basic aqueous layer is extracted with ethyl acetate (2×25 ml). The combined organic layers are dried (sodium sulfate), concentrated, and purified by chromatography (silica gel, 10% methanol/methylene chloride) to afford pure product 9 (52% yield).

Preparation of (2-aminoethyl)[3-(2,4-dichlorophenyl)-4-(morpholin-4-ylmethyl)phenyl]amine (10).

A solution of the Boc material 9 (40 mg) in methanol (1 ml) is treated with 1N HCl in dioxane (1 ml). The solution is stirred at room temperature overnight and evaporated to dryness. The mixture is redissolved in methanol (2 ml) azeotroped with anhydrous toluene (2 ml). The yellow solid is triturated with ether (2×2 ml), ethyl acetate (2×2 ml) and dried in vacuo. The HCl salt of product 10 is not purified further.

Preparation of $N^6$-(2-{[2',4'-dichloro-6-(morpholin-4-ylmethyl)-1,1'-biphenyl-3-yl]-amino}ethyl)-3-nitropyridine-2,6-diamine (12).

The amine hydrochloride salt 10 (35 mg) in acetonitrile (2 ml) is treated with N,N-diisopropylethylamine (54 eq) and 6-chloro-3-nitro-2-pyridylamine 11 (1.2 eq) and stirred at 90° C. for 2 h. The mixture is concentrated under reduced pressure and dried under vacuum. The crude product is purified by chromatography starting with 3% MeOH in methylene chloride and finishing with, 5% MeOH in methylene chloride to provide 12 as yellow solid (50–70%). The material is acidified with 2 equivalents of HCl and lyophilized to a dry powder.

Example 17

Preparation of [5-({2-[(6-amino-5-nitropyridin-2-yl)amino]ethyl}amino)-2',4'-dichloro-1,1'-biphenyl-2-yl](phenyl)methanol (15).

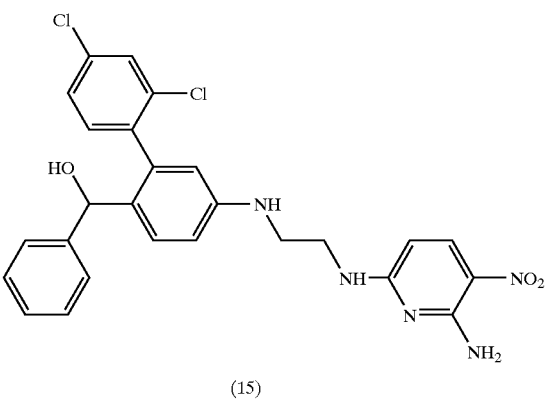

(15)

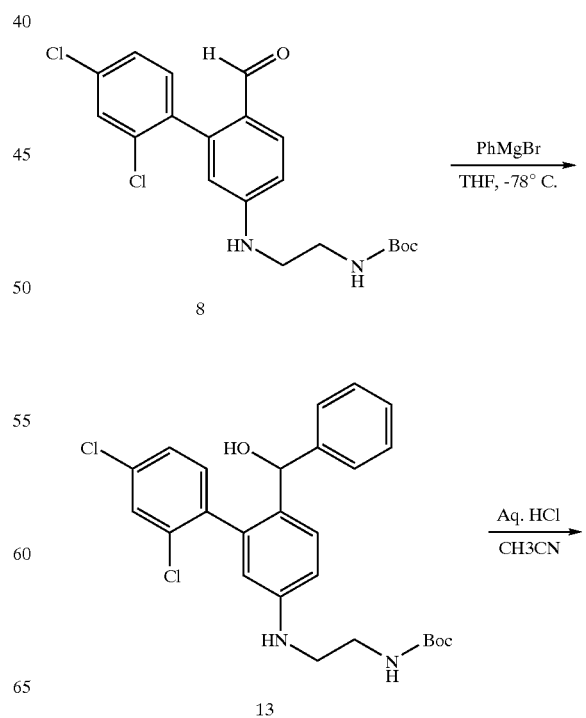

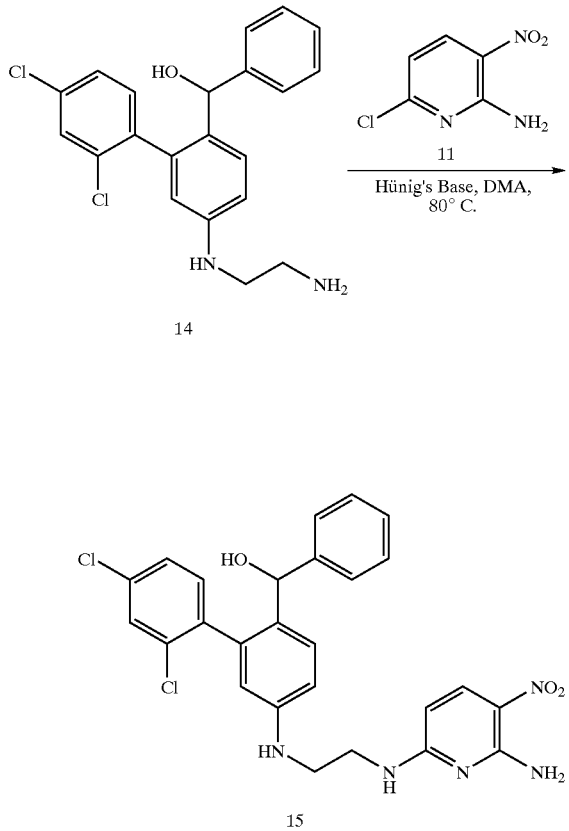

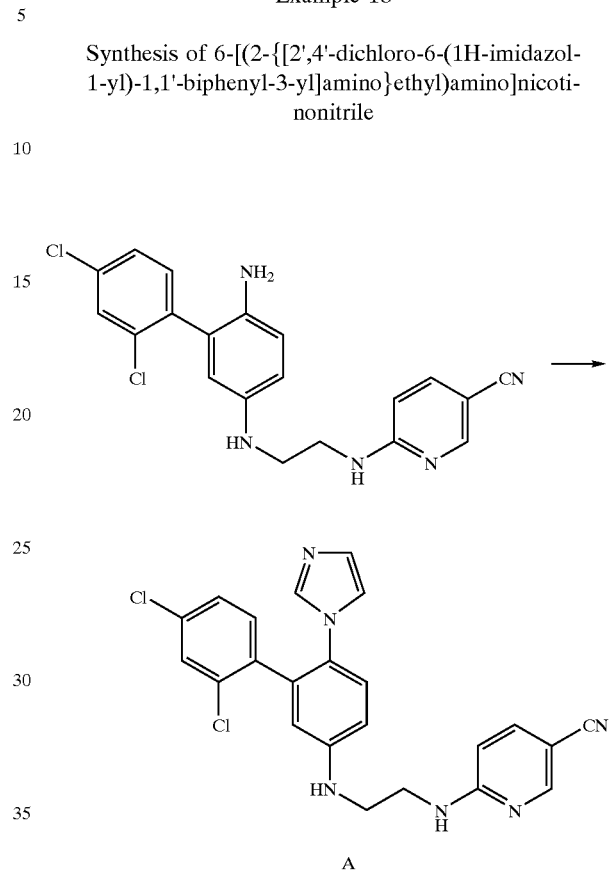

Preparation of N-(2-{[3-(2,4-dichlorophenyl)-4-(hydroxyphenylmethyl)phenyl]-amino}ethyl)(tert-butoxy)carboxamide (13).

Phenylmagnesiumbromide (1M in THF) (2eq) is added to a solution of 8 (50 mg) in THF (10 ml) at 78° C. under argon with stirring. The reaction is allowed to stir for 15 min. at 78° C. after the addition of Grignard at which time sat; aq. NH$_4$Cl (4 ml) is added to quench the reaction. The mixture is diluted with EtOAc (60 ml) and water (2 ml), and the layers are separated. The organic layer is washed with sat. aq. NH$_4$Cl (10 ml), water (10 ml), brine (10 ml), dried (Na$_2$SO$_4$), filtered and concentrated. The residue is purified by silica column chromatography eluting with EtOAc/hexane to give 13.

{4-[(2-aminoethyl)amino]-2-(2,4-dichlorophenyl) phenyl}phenylmethan-1-ol (1 eq) and 6-chloro-3-nitro-2-pyridylamine (1.2 eq) are dissolved in DMA with stirring under argon at rt. Hünig's Base (1.5 eq) is added to the clear dark brown solution which is heated to 80° C. for 12 hours until completion is determined by LC/MS and TLC, eluting with EtOAc/Hexane (3:2, v/v) (R$_f$0.3). EtOAc is added to the reaction mixture which is then washed with water, brine, dried (Na$_2$SO$_4$), filtered, and concentrated to dryness to give the crude-brown product. The brown residue is purified by silica column chromatography eluting with EtOAc/Hexane (24:26, v/v). After collecting the purified fractions and concentrating, the product is isolated as a light yellow solid (75% yield, LCMS m/z MH+525.4).

Example 18

Synthesis of 6-[(2-{[2',4'-dichloro-6-(1H-imidazol-1-yl)-1,1'-biphenyl-3-yl]amino}ethyl)amino]nicotinonitrile 6-[(2-{[2',4'-Dichloro-6-(1H-imidazol-1-yl)-1,1'-biphenyl-3-yl]amino}ethyl)-amino]nicotinonitrile (compound A) may be formed by treating the compound of Example 7 with formaldehyde, glyoxal, and NH$_4$Cl. (Perry, M. C. et al., "Optically Active Iridium Imidazol-2-ylidene-oxazoline Complexes: Preparation and Use in Asymmetric Hydrogenation of Arylalkenes," *J. Am. Chem. Soc.* 125(1): 113–123 (2003)).

Example 19

Synthesis of 6-[(2-{[2',4'-dichloro-6-(2-phenyl-1H-imidazol-1-yl)-1,1'-biphenyl-3-yl]amino}ethyl) amino]nicotinonitrile

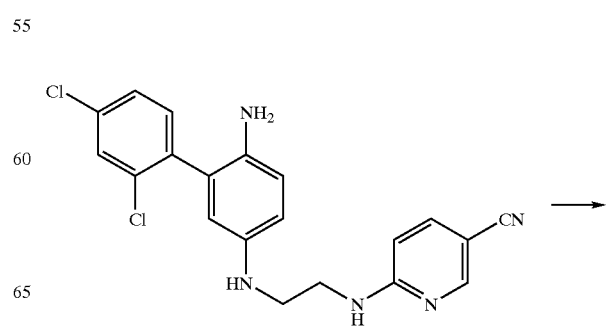

-continued

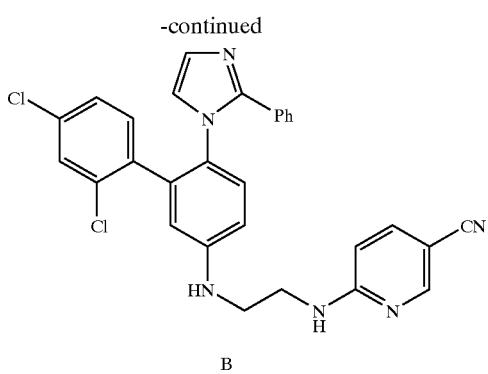

B

6-[(2-{[2',4'-Dichloro-6-(2-phenyl-1H-imidazol-1-yl)-1,1'-biphenyl-3-yl]-amino}ethyl)-amino]nicotinonitrile (compound B) may be formed by treating the compound of Example 7 with benzoyl chloride, 2-aminoacetaldehyde diethyl acetal, PCl$_3$, p-toulenesulfonic acid and hydrogen peroxide (Romine, J. L. et al., "4,5-Diphenyltriazol-3-ones: Openers of Large-Conductance Ca$^{2+}$-Activated Potassium (Maxi-K) Channels," *J. Med. Chem.* 45(14): 2942–2952 (2002)).

Example 20

Synthesis of 6-[(2-{[2',4'-dichloro-6-(1H-imidazol-2-yl)-1,1'-biphenyl-3-yl]amino}ethyl)amino]nicotinonitrile

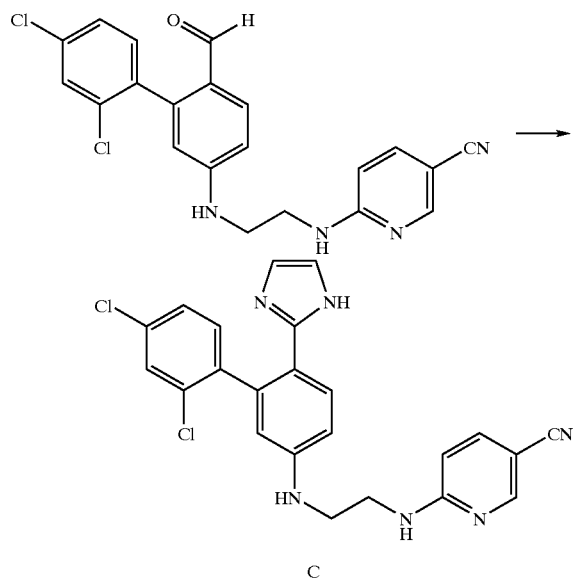

C

6-[(2-{[2',4'-dichloro-6-(1H-imidazol-2-yl) 1,1'-biphenyl-3-yl]amino}ethtl)-amino]nicotinonitrile (compound C) may be formed by treating compound 8 of Example 17 with glyoxal and ammonia (Hagedorn III A. A. et al., "Cardiotonic agents. 2. (Imidazolyl)aroylimidazolones, highly potent and selective positive inotropic agents," *J. Med. Chem.* 30(8): 1342–7 (1987)).

Example 21

Screening for GSK3 Inhibitory Activity Using a Cell-Free Assay

Carbocyclic compounds of the present invention were dissolved in DMSO, then tested for inhibition of human GSK3β (the nucleotide sequence for human GSK3β appears in GenBank under Accession No. L33801). Expression of GSK3β is described, for example, in Hughes et al., *Eur. J. Biochem.*; 203:305–11 (1992), which is incorporated herein by reference.

An aliquot of 300 μl of substrate buffer (30 mM tris-HCl, 10 mM MgCl$_2$, 2 mM DTT, 3 μg/ml GSK3μ and 0.5 μM biotinylated prephosphorylated SGSG-linked CREB peptide (Chiron Technologies PTY Ltd., Clayton; Australia) was dispensed into wells of a 96 well polypropylene microtiter plate. 3.5 μl/well of DMSO containing varying concentrations of each compound to be assayed or staurosporine (a known kinase inhibitor used as a positive control, or a negative control (i.e., DMSO only), was added and mixed thoroughly. The reactions were then initiated by adding 50 μl/well of 1 μM unlabeled ATP and 1–2×10$^7$ cpm γ$^{33}$P-labeled ATP, and the reaction was allowed to proceed for about three hours at room temperature.

While the reaction was proceeding, streptavidin-coated Labsystems "Combiplate 8" capture plates (Labsystems, Helsinki, Finland) were blocked by incubating them with 300 μl/well of PBS containing 1% bovine serum albumin for at least one hour at room temperature. The blocking solution was then removed by aspiration, and the capture plates were filled with 100 μl/well of stopping reagent (50 μM ATP/20 mM EDTA).

When the three hour enzyme reaction was finished, triplicate 100 μl aliquots of each reaction mix were transferred to three wells containing stopping solution, one well on each of the three capture plates, and the well contents were mixed well. After one hour at room temperature, the wells of the capture plates were emptied by aspiration and washed five times using PBS and a 12 channel Corning 430474 ELISA plate washer. Finally, 200 μl of Microscint-20 scintillation fluid was added to each well of the plate. The plates were coated with plate sealers, then left on a shaker for 30 minutes. Each capture plate was counted in a Packard TopCount scintillation counter (Meridian, Conn.) and the results were plotted as a function of compound concentration.

Compounds of the present invention were then screened for inhibitory activity against GSK3 according to this assay. The compounds of Examples 3–11 exhibited IC$_{50}$s of 1 μM or less with respect to GSK3 in this cell-free assay.

Accordingly, these results demonstrate that compounds of the present invention exhibit inhibitory activity against GSK3.

Example 22

Screening for GSK3 Inhibitory Activity Using a Cell-Based Glycogen Synthase Assay CHO-HIRC cells are maintained in 10 cm tissue culture plates in Ham's F12 medium/10% dialyzed fetal bovine serum. Cells from a confluent 10 cm plate are harvested and divided into the 6 wells of a 6-well tissue culture plate to a final volume of 2 ml of medium. The cells are left to grow at 37° C. for 24 hours. The cells are then washed three times in Ham's F12 medium containing no fetal bovine serum, and finally the cells are left for a further 24 hours at 37° C. in 2 ml of the serum-free medium.

At the end of this time, 20 µl of compound dissolved in DMSO is added to each well and incubated at 37° C. After 20 minutes the medium is removed and the cells are washed once in PBS at room temperature and then rapidly frozen in the plates in liquid nitrogen. Cells are then thawed on ice in the presence of 140 µl of lysis buffer (50 mM Tris pH 7.8; 1 mM EDTA, 100 mM NaF, 25 µg/ml leupeptin, 1 mM DTT, 1 mM PMSF) per well. Cells are scraped from the plates and frozen in Eppendorf tubes on dry ice. Lysates are then thawed and refrozen on dry ice.

After rethawing, lysates are spun at 14,000 g for 15 minutes. The supernatants are then removed and stored on ice. Each supernatant (45 µl) is added to 45 µl of reaction buffer (65 mM Tris pH 7.8; 26 mM EDTA, 32.5 mM KF, 9.3 mM UDP-glucose; 11 mg/ml glycogen; 500 nCi/ml $^{14}$C-UDP-glucose) and a further 45 µl is added to 45 µl reaction buffer/20 mM glucose-6-phosphate. Reactions are incubated at 30° C. for 30 minutes and then spotted onto a 2 cm square 31ET chromatograph paper (Whatman). Filter papers are washed twice for 20 minutes in 66% ethanol, rinsed briefly in acetone and dried for 1 hour at room temperature.

Filters are added to 5 ml of liquid scintillant and counted in a liquid scintillation counter. The percentage of the total glycogen synthase that is active in any lysate is expressed as 100× (cpm minus glucose-6-phosphate)/(cpm plus glucose-6-phosphate). Such values are determined in duplicate for 5 different concentrations of compound and for DMSO alone, and the values are then plotted against the logarithm of the concentration. The concentration of compound that stimulates glycogen synthase activity to 50% of the maximal level is determined by fitting a sigmoidal curve to the plotted data. The maximal level is defined as that level to which glycogen synthase activity tends asymtotically as the concentration of test compound increases substantially beyond the $EC_{50}$.

Example 23

Screening for Inhibition of Tau Protein Phosphorylation

A. Transient Transfection of COS Cells with GSK3 Expression Plasmid and Tau Expression Plasmid Construction COS cells are maintained in T25 tissue culture flasks in high glucose MEM medium/5% fetal bovine serum. Cells from a confluent T25 flask are harvested and 80,000 cells/well are seeded into Corning 6-well tissue culture plates' in a final volume of 2 ml/well of medium. The cells are left to grow at 37° C. for 48 hours. The cells are then washed twice in Opti-MEM containing no fetal bovine serum, and finally the cells are left in 1 ml of Opti-MEM.

Polynucleotide encoding tau protein is subcloned into plasmid pSG5 under an early SV40 promoter to generate a tau expression plasmid. The cloning of cDNA encoding tau protein is generally described in Goedert et al., *EMBO Journal*, 8(2):393–399 (1989), which is incorporated herein by reference. A GSK3 expression plasmid is prepared by subcloning polynucleotide encoding GSK3β into pCG, which is an ApEVRF derivative described in Giese et al., *Genes & Development*, 9:995–1008 (1995) and Matthias et al., *Nucleic Acid Research*, 17:6418 (1989), both of which are incorporated herein by reference.

The following solutions are prepared in 1.5 ml Eppendorf tubes: Solution A: for each transfection, 2 µg of DNA (tau expression plasmid) and 0.7 µg of DNA (GSK3 expression plasmid) are diluted into 100 µl of Opti-MEM (Gibco BRL);

Solution B: for each transfection, 8 µl of Lipofectamine reagent is diluted into 100 µl of Opti-MEM. The two solutions are combined, mixed gently, and incubated at room temperature for 45 minutes to allow DNA-liposome complexes to form. For each transfection, 0.8 ml of Opti-MEM is added to the tube containing the complexes. The diluted solution is mixed gently and overlaid onto the rinsed cells. The cells are incubated with the complexed DNA/Lipofectamine for 6 hours at 37° C. in a $CO_2$ incubator. Following incubation, 1 ml of growth medium (high glucose MEM) with 20% FBS is added to each well and incubated at 37° C. overnight. The medium is replaced with fresh, complete medium at 18 hours following the start of transfection, and the cells are left to grow at 37° C. for another 48 hours.

B. Tau Phosphorylation Inhibition Assay

Two hours before harvesting, 2 µl of test compound (GSK3 inhibitor) dissolved in DMSO is added to each well and incubated at 37° C. After 2 hours the medium is removed and the cells are rapidly frozen on the plates on dry ice and stored at −70° C. Cells are thawed on ice in the presence of 200 µl of lysing buffer (1% Triton® X-100, 20 mM Tris pH 7.5, 137 mM NaCl, 15% glycerol, 25 µg/ml leupeptin, 1 µg ml pepstatin-A, 1 µM PMSF, 21 µg/ml aprotinin, 0.50 mM NaF, 50 mM β-glycerophosphate, 15 mM sodium pyrophosphate, 1 mM sodium orthovanadate). The contents of each well are centrifuged at 14,000 g, 4° C. for 5 minutes and the supernatants transferred to clean tubes. At this point the lysates may be stored at −20° C.

C. ELISA to Detect Phosphorylated Tau in Cell Lysates

Immulon 4 strips (Dynatech) are coated with monoclonal anti-phosphorylated tau (AT8, Polymedco, Inc.) at 5 µg/ml in PBS containing $Ca^{++}$ and $Mg^{++}$, 100 µl/well. After overnight incubation at 4° C., the strips are washed twice with washing buffer (PBS containing 0.05% Tween® 20) and blocked with PBS containing 1% BSA, 5% normal mouse serum and 0.05% Tween® 20 at room temperature for 1 hour. The strips are washed 5 times with washing buffer. Lysate (100 µl) diluted 1:10 in PBS containing 1% BSA, 0.1% $NaN_3$ is added into each well and incubated at room temperature for 1 hour. After washing, 100 µl of 0.5 µg/ml biotinylated monoclonal anti-(non-phosphorylated) tau (HT7, Polymedco; Inc.) in PBS-BSA is added into each well. Strips are washed 5 times and HRP-conjugated streptavidin is added, incubated at room temperature for 30 minutes and washed extensively with washing buffer. TMB substrate (Pierce) is used for color development and the reaction is stopped by adding an equal volume of 0.8 M sulfuric acid. Strips are read on an ELISA plate reader using a 450 nm filter. The concentration of compound that inhibits tau phosphorylation to 50% of the maximal level (i.e., $IC_{50}$) is determined by fitting a sigmoidal curve to the plotted data.

Example 24

Testing the Potential of GSK3 Inhibitors to Protect Primary Hippocampal Cells from Glutamate Excitotoxicity Hippocampi are dissected from embryonic day 18–19 rats. The tissue is collected in Hibernate™ media (Gibco BRL) and minced into approximately 1 mm pieces. Tissue is dissociated using the Papain Dissociation System (Worthington Biochemical Corporation). Following isolation the cells are resuspended in serum-free media composed of Neurobasal™ (Gibco BRL), 2% B27 supplement (Gibco-BRL), L-glutamine and antibiotics. Cells are plated in 35 mm tissue culture dishes' coated with poly-L-lysine at a concentration of $7.5 \times 10^4$ cells per dish. Following 10–14 days at 37° C. in 5% $CO_2$ cells are rinsed and fed with fresh media. The next day representative compounds of the invention are added to the culture media to a final concentration of between 1 nM and 100 µM. Four to eight hours following compound addition the conditioned media is removed from cells and stored at 37° C. Cultures are rinsed twice with HEPES-buffered balanced salt solution (HBSS) containing 10 µM glycine. Grabb and Choi, *J. Neuroscience* 19:1657–62 (1999). Cultures are then exposed for 5 min at room temperature to 200 µM glutamic acid in the same HBSS. Following exposure, cultures are rinsed three times with the buffer and then returned to their original conditioned media containing the compounds. Twenty to twenty-four hours following glutamic acid exposure, cultures are rinsed in HBSS and exposed for 10 min to Trypan Blue. This dye is taken up by dead cells. The cultures are rinsed and then fixed for 30 min in 4% paraformaldehyde. The number of live and dead (blue nuclei) large neurons are counted (at least 200 cells from each culture) by phase contrast microscopy and photographed. Using this method, compounds of this invention are shown to be capable of significantly reducing the potential of glutamate to induce neuronal cell death.

Example 25

Evaluation of Efficacy in Diabetic Rodents (The Glucose Tolerance Test)

Compound Formulation for Oral Dosing:

Test compounds are typically formulated for oral gavage as solutions in water or suspensions in 1% carboxymethylcellulose/0.1% tween-80 (both from Sigma Chem., MO) the day prior to administration. Test compounds can also be formulated as solutions in 15% Captisol (a modified cyclodextrin by CyDex Co., IL) following procedures common to those below. For water solutions, dry and lyophilized test compound powder is solubilized in distilled water and mixed well by vortexing and sonicating. If necessary, test solution is pH adjusted with 1 N NaOH or 1 N HCl and is finally sterile filtered through a syringe appended with a 0.2 micron cellulose acetate membrane (Millipore Co., MA). For oral suspensions, the test compound powder is mixed with a fresh suspension of 1% carboxymethylcellulose/0.1% tween-80 and extensively sonicated, pH adjusted if necessary as described above, and vortexed until particle size is homogeneous and <10 micron in size.

Diabetic Mouse Glucose Tolerance Test:

Obese db/db (female C57BlKs/J) mice are obtained from Jackson Labs (Bar Harbor, Me.) at 8 weeks of age and used for efficacy testing 1–2 weeks later. On the morning of a test, food is removed early in the morning (7–8 hrs prior to the glucose bolus). Local anesthetic (EMLA creme, Astra Pharm., MA) is applied to the end of the tail and 50–100 µl blood samples are obtained from snips of the tail tip and collected into eppendorf tubes containing 5 µl 500 U/ml sodium heparin (Elkins-Sinn, NJ) with subsequent isolation of plasma. Samples are obtained at various intervals throughout the day for a total of 6–8 time points. Mice are randomized into treatment groups and administered the first oral dose of test compound (0.2 ml volume) 4.5 hr prior to the glucose and again 0.5 hr prior to administration of 0.2 ml 50% dextrose (Abbott Lab., IL) via oral gavage (oGTT) or intraperitoneal injection. After the final blood sample about 2 hr following the glucose administration, food is returned to the animals.

Regulation of Basal Glycemia and Insulinemia:

Test compounds are typically orally administered to db/db mice (see above) or ZDF rats (Genetic Models, Inc.; Indianapolis, Ind.) in the context of a multi-day, multi-dose regimen or as a single bolus. The ZDF rats are received at 8 weeks of age and used for efficacy testing 1–2 weeks later. Food is removed about 30 min prior to dosing and a single bolus of test compound (dosing volume ranging from 1–8 mg/ml) is administered. Blood is sampled as described above at 1–6 time points over the next 2–3 hr. Food is returned to the animal cages following the blood sampling.

Primary Endpoints:

Glucose and insulin levels are measured from plasma and/or blood samples. Glucose levels are measured from whole blood by the One-Touch glucometer (Lifescan Co., CA) and from plasma by Beckman glucose analyzer. Glucose results typically reflect blood values for mouse and plasma values for rat studies. Measurement of insulin levels is made via ELISA (Crystal Chem. Co. IL) following the supplier's protocol.

Results Quantitation:

Efficacy may be expressed as mg/dL glucose or ng/ml insulin or represented as area under the curve (AUC) for plasma glucose (taken above the normoglycemic baseline of 100 mg/dL) and insulin (taken above the normoinsulinemic baseline of 1 ng/mL). Typically, when expressed as AUC, the results are actually represented as reduced AUC ([(vehicle control AUC—test group AUC)/vehicle control AUCX100]). Such expression provides a single quantitative expression of the magnitude of improved glucose disposal and/or reduced basal hyperglycemia or insulin conservation relative to the placebo control group.

Results:

Representative compounds of the invention are expected to exhibit good in vitro potency, and when formulated in captisol and administered s.c. to mice (30 mg/kg), to exhibit high bioavailability and tissue penetration in vivo. A significant reduction in basal hyperglycemia just prior to the glucose tolerance test, and significantly improved glucose disposal following glucose challenge are expected to be observed. A significant reduction in the AUC relative to the control group is expected if the glucose response is quantitated by determining the area under the blood glucose curve (AUC) from −60 min to +120 min. This is comparable to the efficacy obtained with Troglitazone (when dosed orally for at least several days at either 60 or 100 mg/kg/day). Also of significance is the expectation that insulin levels in treated animals remain lower than in control mice.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the structure:

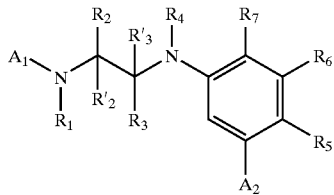

wherein:
- $A_1$ and $A_2$ are optionally substituted aryl, arylamino, aryloxy or heteroaryl;
- $R_1$, $R_2$, $R_3$ and $R_4$ are independently selected from the group consisting of hydrogen, hydroxyl, and optionally substituted loweralkyl, cycloloweralkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;
- $R'_2$ and $R'_3$ are independently selected from the group consisting of hydrogen, and optionally substituted loweralkyl;
- $R_5$, $R_6$ and $R_7$ are independently selected from the group consisting of hydrogen, hydroxy, halo, carboxyl, nitro, amino, amido, amidino, imido, cyano, and substituted or unsubstituted loweralkyl, loweralkoxy, alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, arylamino, aralkylamino, heteroarylamino, heteroaralkylamino, alkylcarbonylamino, alkylaminocarbonylamino, arylaminocarbonylamino, aralkylcarbonylamino, heteroaralkylcarbonylamino, arylcarbonylamino, heteroarylcarbonylamino, amidino, cycloalkyl, cycloamido, cyclothioamido, cycloamidino, heterocyclyl, heterocycloamidino, cycloimido, heterocycloimido, guanidinyl, aryl, biaryl, heteroaryl, heterobiaryl, heterocyclo, heterocycloalkyl, arylsulfonyl and arylsulfonamido;

and the pharmaceutically acceptable salts thereof.

2. A compound of claim 1, wherein at least one of $A_1$ and $A_2$ comprises an aromatic ring having from 3 to 10 carbon ring atoms and optionally 1 or more ring heteroatoms.

3. A compound of claim 2, wherein at least one of $A_1$ and $A_2$ is optionally substituted carbocyclic aryl, arylamino or aryloxy.

4. A compound of claim 2, wherein at least one of $A_1$ and $A_2$ is optionally substituted heteroaryl.

5. A compound of claim 2, wherein at least one of $A_1$ and $A_2$ is selected from the group consisting of substituted or unsubstituted phenyl, phenylamino, phenyloxy, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl.

6. A compound of claim 2, wherein at least one of $A_1$ and $A_2$ is substituted with at least one and not more than 3 substitution groups.

7. A compound of claim 6, wherein said substitution groups are independently selected from the group consisting of nitro, amino, cyano, halo, thioamido, amidino, oxamidino, alkoxyamidino, imidino, guanidino, sulfonamido, carboxyl, formyl, loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aminoalkyl and cyanoalkyl.

8. A compound of claim 4 wherein $A_1$ has the formula:

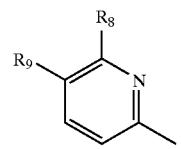

wherein $R_8$ and $R_9$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl.

9. A compound of claim 8, wherein $A_1$ is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl.

10. A compound of claim 1, wherein at least one of $R_1$, $R_2$, $R_3$ and $R_4$ is substituted loweralkyl selected from the group consisting of haloloweralkyl, heterocycloaminoalkyl, and loweralkylaminoloweralkyl.

11. A compound of claim 10, wherein at least one of $R_1$, $R_2$, $R_3$ and $R_4$ is loweralkylaminoloweralkyl.

12. A compound of claim 10, wherein $R_1$, $R_2$, and $R_3$ are hydrogen and $R_4$ is selected from the group consisting of hydrogen, methyl, ethyl, aminoethyl, dimethylaminoethyl, pyridylethyl, piperidinylethyl, pyrrolidinyl ethyl, piperazinylethyl and morpholinylethyl.

13. A compound of claim 1, wherein at least one of $R_5$, $R_6$ and $R_7$ is selected from the group consisting of substituted and unsubstituted aryl, heteroaryl and biaryl.

14. A compound of claim 13 wherein at least one of $R_5$, $R_6$ and $R_7$ is a substituted or unsubstituted moiety of the formula:

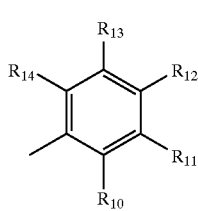

wherein $R_{10}$, $R_{11}$, $R_{12}$, $R_{13}$, and $R_{14}$ are independently selected from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, alkylthio, alkylcarbonylamino, aralkylcarbonylamino, heteroaralkylcarbonylamino, arylcarbonylamino, heteroarylcarbonylamino aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyloxyalkyl, and heteroaralkcarbonyloxyalkyl.

15. A compound of claim 14 wherein $R_{10}$, $R_{11}$, $R_{13}$, and $R_{14}$ are hydrogen and $R_{12}$ is selected from the group consisting of halo, loweralkyl, hydroxy, loweralkoxy, haloloweralkyl, aminocarbonyl, alkylaminocarbonyl, morpholino, piperidino and cyano.

16. A compound of claim 14 wherein $R_{11}$, $R_{13}$, and $R_{14}$ are hydrogen and $R_{10}$ and $R_{12}$ are independently selected from the group consisting of halo, loweralkyl, hydroxy, loweralkoxy, haloloweralkyl, morpholino, piperidino and cyano.

17. A compound of claim 14 wherein $R_{10}$, $R_{11}$, $R_{13}$, and $R_{14}$ are hydrogen and $R_{12}$ is heteroaryl.

18. A compound of claim 14 wherein $R_{10}$, $R_{11}$, $R_{13}$, and $R_{14}$ are hydrogen and $R_{12}$ is a heterocycloalkyl.

19. A compound of claim 14 wherein at least one of $R_{10}$, $R_{11}$, $R_{12}$, $R_{13}$, and $R_{14}$ are halo and the remainder of $R_{10}$, $R_{11}$, $R_{12}$, $R_{13}$, and $R_{14}$ are hydrogen.

20. A compound of claim 14 wherein at least one of $R_{10}$, $R_{11}$, $R_{12}$, $R_{13}$, and $R_{14}$ are selected from the group consisting of morpholino, piperidino, and the remainder of $R_{10}$, $R_{11}$, $R_{12}$, $R_{13}$, and $R_{14}$ are hydrogen.

21. A compound of claim 14 wherein at least one of $R_5$, $R_6$ and $R_7$ is selected from the group consisting of dichlorophenyl, difluorophenyl, trifluoromethylphenyl, chlorofluorophenyl, bromochlorophenyl, bromofluorophenyl, ethylphenyl, methylchlorophenyl, ethylchlorophenyl, imidazolylphenyl, cyanophenyl, morphlinophenyl and cyanochlorophenyl.

22. A compound of claim 1, wherein $R_6$ is substituted alkyl selected from the group consisting of aralkyl, hydroxyalkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

23. A compound of claim 1, wherein $R_6$ is substituted amino selected from the group consisting of alkylamino, alkylcarbonylamino, alkoxycarbonylamino, arylalkylamino, arylcarbonylamino, alkylthiocarbonylamino, arylsulfonylamino, heteroarylamino, alkylcarbonylamino, arylcarbonylamino, heteroarylcarbonylamino, aralkylcarbonylamino, and heteroaralkylcarbonylamino.

24. A compound of claim 1, wherein $R_6$ is selected from the group consisting of unsubstituted or substituted aminocarbonyl, alkyloxycarbonyl, aryloxycarbonyl, aralkyloxycarbonyl and alkylaminoalkyloxycarbonyl.

25. A compound of claim 1, wherein $R_6$ is selected from the group consisting of amidino, guanidino, cycloimido, heterocycloimido, cycloamido, heterocycloamido, cyclothioamido and heterocycloloweralkyl.

26. A compound of claim 1, wherein $R_6$ is aryl.

27. A compound of claim 1, wherein at least one of $R_5$, $R_6$ and $R_7$ is a substituted or unsubstituted heteroaryl or heterocyclyl group.

28. A compound of claim 27, wherein at least one of $R_5$, $R_6$ and $R_7$ is selected from the group consisting of substituted or unsubstituted pyridyl, pyrimidinyl, pyrrolidinyl, pyrrolinyl, pyrazinyl, thiazolyl, indolyl, imidazolyl, imidazolidinyl, oxadiazolyl, oxazolidinyl, oxazolidinonyl, tetrazolyl, pyrazinyl, pyrazolidinyl, piperidyl, piperazinyl, morpholinyl, triazolyl, thienyl, furanyl, quinolinyl, pyrrolylpyridyl, pyrazolonyl, pyridazinyl, benzothiazolyl, benzopyridyl, benzotriazolyl, and benzimidazolyl.

29. A compound of claim 28 wherein at least one of $R_5$, $R_6$ and $R_7$ is a monoketopiperazinyl group having the structure:

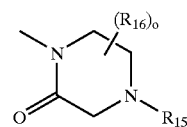

(IV)

wherein $R_{15}$ and $R_{16}$ are independently selected from the group consisting of hydrogen, loweralkyl, loweralkynyl, aryl, heteroaryl, arylloweralkyl, loweralkylarylloweralkyl, haloloweralkyl, haloarylloweralkyl carbocyclic and heterocyclic; or $R_{16}$ can be taken with another $R_{16}$ or with $R_{15}$ to form a carbocyclic, heterocyclic or aryl ring; and o is an integer between 1 and 3.

30. A compound of claim 29, wherein $R_{15}$ is loweralkyl.

31. A compound of claim 30, wherein $R_{15}$ is selected from the group consisting of methyl, ethyl, n-propyl, isopropyl, cyclopropyl, n-butyl, iso-butyl and t-butyl.

32. A compound of claim 29, wherein $R_{15}$ is taken with $R_{16}$ to form a group having the structure:

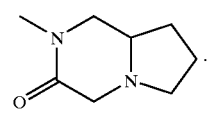

(V)

33. A compound of claim 29, wherein $R_{15}$ is taken with $R_{16}$ to form a group having the structure:

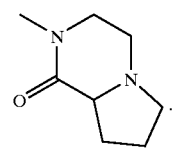

(VI)

34. A composition comprising an amount of a compound of claim 1 effective to modulate GSK3 activity in a human or animal subject when administered thereto, together with a pharmaceutically acceptable carrier wherein said GSK3 mediated disorder is select from the group consisting of diabetes, Alzheimer's disease, Parkinson's disease, Huntington's disease, obesity, atherosclerotic cardiovascular disease, essential hypertension, polycystic ovary syndrome X, ischemia, traumatic brain injury, bipolar disorder, immunodeficiency and cancer.

35. A method of inhibiting GSK3 activity in a human or animal subject, comprising administering to the human or animal subject a composition of claim 29 wherein said GSK3 mediated disorder is select from the group consisting of diabetes, Alzheimer's disease, Parkinson's disease, Huntington's disease, obesity, atherosclerotic cardiovascular disease, essential hypertension, polycystic ovary syndrome X, ischemia, traumatic brain injury, bipolar disorder, immunodeficiency and cancer.

36. A method of treating a cell comprising administering to the cell an amount of a compound of claim 1 effective to inhibit GSK3 activity in the cell.

37. A method for treating a GSK3-mediated disorder in a human or animal subject, comprising administering to the human or animal subject an amount of a composition of claim 34 effective to inhibit GSK3 activity in the subject wherein said GSK3 mediated disorder is select from the group consisting of diabetes, Alzheimer's disease, Parkinson's disease, Huntington's disease, obesity, atherosclerotic cardiovascular disease, essential hypertension, polycystic ovary syndrome X, ischemia, traumatic brain injury, bipolar disorder, immunodeficiency and cancer.

38. A method of claim 37, wherein the composition is administered by a mode of administration selected from the group consisting of oral, subcutaneous, transdermal, transmucosal, iontophoretic, intravenous, intrathecal, buccal, sublingual, intranasal, and rectal administration.

39. A method of claim 37, which further comprises administering to the subject one or more additional active agents.

40. A method of claim 37, wherein the GSK3-mediated disorder is diabetes and the additional active agent is selected from the group consisting, of insulin, troglitazone, rosiglitazone, pioglitazone, glipizide and metformin.

* * * * *

UNITED STATES PATENT AND TRADEMARK OFFICE
CERTIFICATE OF CORRECTION

PATENT NO. : 6,989,382 B2
APPLICATION NO. : 10/690497
DATED : January 24, 2006
INVENTOR(S) : A.S. Wagman et al.

It is certified that error appears in the above-identified patent and that said Letters Patent is hereby corrected as shown below:

| COLUMN | LINE | |
|---|---|---|
| 50 | 45 | "pyrrolidinyl ethyl," should read --pyrrolidinylethyl,-- |
| 52 | 56 | "is select from" should read --is selected from-- |
| 52 | 65 | "is select from" should read --is selected from-- |
| 53 | 11 | "is select from" should read --is selected from-- |
| 54 | 12 | after "consisting" delete "," |

Signed and Sealed this

Eighth Day of May, 2007

JON W. DUDAS
*Director of the United States Patent and Trademark Office*